(12) United States Patent
Martin et al.

US008889400B2

(10) Patent No.: US 8,889,400 B2
(45) Date of Patent: Nov. 18, 2014

(54) DILUTING EXHAUST GAS BEING SUPPLIED TO BIOREACTOR

(75) Inventors: Steven C. Martin, Toronto (CA); Max Kolesnik, Schomberg (CA); Jaime A. Gonzalez, Oakville (CA)

(73) Assignee: Pond Biofuels Inc., Scarborough (CA)

( * ) Notice: Subject to any disclaimer, the term of this patent is extended or adjusted under 35 U.S.C. 154(b) by 384 days.

(21) Appl. No.: 12/784,126

(22) Filed: May 20, 2010

(65) Prior Publication Data

US 2011/0287525 A1 Nov. 24, 2011

(51) Int. Cl.
*C12N 1/12* (2006.01)
*C12N 13/00* (2006.01)
*C12M 1/00* (2006.01)

(52) U.S. Cl.
CPC . *C12N 1/12* (2013.01); *Y02E 50/10* (2013.01); *C12N 13/00* (2013.01); *Y02E 50/30* (2013.01); *C12M 43/06* (2013.01); *C12M 21/02* (2013.01)
USPC .................................................. 435/257.1

(58) Field of Classification Search
None
See application file for complete search history.

(56) References Cited

U.S. PATENT DOCUMENTS

| | | |
|---|---|---|
| 2,658,310 A | 11/1953 | Cook |
| 2,715,795 A | 8/1955 | Pallotta et al. |
| 2,732,661 A | 1/1956 | Spoehr et al. |
| 2,732,663 A | 1/1956 | Dewey |
| 2,815,607 A | 12/1957 | Schroeder |
| 2,854,792 A | 10/1958 | Juda |
| 3,224,143 A | 12/1965 | Tew et al. |
| 3,243,918 A | 4/1966 | Machiedo |
| 3,303,608 A | 2/1967 | Hannan |
| 3,403,471 A | 10/1968 | Clement et al. |
| 3,504,185 A | 3/1970 | Zweig |
| 3,650,068 A | 3/1972 | Meyer et al. |
| 3,712,025 A | 1/1973 | Wallace |
| 3,763,824 A | 10/1973 | Schoon |
| 3,855,121 A | 12/1974 | Gough |
| 3,882,635 A | 5/1975 | Yamanaka et al. |
| 3,959,923 A | 6/1976 | Selke |
| 3,986,297 A | 10/1976 | Ichimura et al. |
| 4,043,903 A | 8/1977 | Dor |
| 4,078,331 A | 3/1978 | Savins et al. |
| 4,084,346 A | 4/1978 | Stengel et al. |
| 4,087,936 A | 5/1978 | Savins et al. |
| 4,116,778 A | 9/1978 | Belousov et al. |
| 4,235,043 A | 11/1980 | Harasawa et al. |
| 4,253,271 A | 3/1981 | Raymond |
| 4,267,038 A | 5/1981 | Thompson |
| 4,297,000 A | 10/1981 | Fries |
| 4,324,068 A | 4/1982 | Anthony |
| 4,341,038 A | 7/1982 | Bloch et al. |
| 4,383,039 A | 5/1983 | Leavitt |
| 4,398,926 A | 8/1983 | Doshi |
| 4,417,415 A | 11/1983 | Cysewski et al. |
| 4,438,591 A | 3/1984 | Kessler |
| 4,442,211 A | 4/1984 | Greenbaum |
| 4,473,970 A | 10/1984 | Hills |
| 4,525,031 A | 6/1985 | Mori |
| 4,539,625 A | 9/1985 | Bornstein et al. |
| 4,595,405 A | 6/1986 | Agrawal et al. |
| 4,626,065 A | 12/1986 | Mori |
| 4,676,956 A | 6/1987 | Mori |
| 4,681,612 A | 7/1987 | O'Brien et al. |
| 4,724,214 A | 2/1988 | Mori |
| 4,781,843 A | 11/1988 | Baker et al. |
| 4,851,339 A | 7/1989 | Hills |
| 4,865,969 A | 9/1989 | Amen et al. |
| 4,869,017 A | 9/1989 | Bird et al. |
| 4,889,812 A | 12/1989 | Guinn et al. |
| 4,900,678 A | 2/1990 | Mori |
| 4,939,087 A | 7/1990 | Van Wie et al. |
| 4,952,511 A | 8/1990 | Radmer |
| 4,958,460 A | 9/1990 | Nielson et al. |
| 4,970,166 A | 11/1990 | Mori |
| 5,040,486 A | 8/1991 | Pack |
| 5,081,036 A | 1/1992 | Familletti |
| 5,104,803 A | 4/1992 | Delente |
| 5,151,342 A | 9/1992 | Wiedemann |
| 5,151,347 A | 9/1992 | Delente et al. |
| 5,206,173 A | 4/1993 | Finn |
| 5,216,976 A | 6/1993 | Marinkovich |
| 5,330,915 A | 7/1994 | Wilson et al. |
| 5,334,497 A | 8/1994 | Inaba et al. |

(Continued)

FOREIGN PATENT DOCUMENTS

| | | |
|---|---|---|
| CA | 2738397 | 11/2011 |
| CA | 2738410 | 11/2011 |

(Continued)

OTHER PUBLICATIONS

Matthijs et al. "Application of light emitting diodes in bioreactors: flashing light effects and energy economy in algal culture." *Biotechnol. Bioeng.* [Online] 2000, 50, pp. 98-107.

(Continued)

*Primary Examiner* — Allison Fox
*Assistant Examiner* — Yvonne Pyla
(74) *Attorney, Agent, or Firm* — Haynes and Boone, LLP

(57) ABSTRACT

There is provided a process of growing a phototrophic biomass in a reaction zone. Prior to supplying a reaction zone feed material, including gaseous exhaust from a gaseous exhaust material producing process, supplying the reaction zone feed material with a supplemental gaseous dilution agent, wherein the carbon dioxide concentration of the supplemental gaseous dilution agent is less than the carbon dioxide concentration of the gaseous exhaust material which is supplied to the reaction zone feed material.

14 Claims, 1 Drawing Sheet

(56) References Cited

U.S. PATENT DOCUMENTS

| | | | |
|---|---|---|---|
| 5,358,858 A | 10/1994 | Chiang et al. |
| 5,424,209 A | 6/1995 | Kearney |
| 5,447,629 A | 9/1995 | Chaumont et al. |
| 5,534,404 A | 7/1996 | Laurance et al. |
| 5,534,417 A | 7/1996 | Arad et al. |
| 5,541,056 A | 7/1996 | Huntley et al. |
| 5,552,058 A | 9/1996 | Fanning |
| 5,558,984 A | 9/1996 | Young et al. |
| 5,565,108 A | 10/1996 | Dimesky et al. |
| 5,573,669 A | 11/1996 | Jensen |
| 5,578,472 A | 11/1996 | Ueda et al. |
| 5,614,378 A | 3/1997 | Yang et al. |
| 5,656,421 A | 8/1997 | Gebhard et al. |
| 5,659,977 A | 8/1997 | Jensen et al. |
| 5,670,046 A | 9/1997 | Kimmel |
| 5,682,709 A | 11/1997 | Erickson |
| 5,686,299 A | 11/1997 | Colwell et al. |
| 5,711,983 A | 1/1998 | Kyle et al. |
| 5,741,702 A | 4/1998 | Lorenz |
| 5,744,041 A | 4/1998 | Grove |
| 5,776,349 A | 7/1998 | Guelcher et al. |
| 5,843,762 A | 12/1998 | Moll |
| 5,846,435 A | 12/1998 | Haase |
| 5,846,816 A | 12/1998 | Forth |
| 5,851,398 A | 12/1998 | Adey |
| 5,871,952 A | 2/1999 | Ghirardi et al. |
| 5,882,849 A | 3/1999 | Leonard et al. |
| 5,897,997 A | 4/1999 | Louvel |
| 5,906,750 A | 5/1999 | Haase |
| 5,910,254 A | 6/1999 | Guelcher et al. |
| 5,912,113 A | 6/1999 | Nakamura et al. |
| 5,951,875 A | 9/1999 | Kanel et al. |
| 5,958,761 A | 9/1999 | Yogev et al. |
| 5,981,260 A | 11/1999 | Metz |
| 5,981,271 A | 11/1999 | Doucha et al. |
| 5,994,129 A | 11/1999 | Armstrong et al. |
| 6,000,551 A | 12/1999 | Kanel et al. |
| 6,022,701 A | 2/2000 | Boussiba et al. |
| 6,083,740 A | 7/2000 | Kodo et al. |
| 6,110,370 A | 8/2000 | Van Hille et al. |
| 6,120,690 A | 9/2000 | Haase |
| 6,128,135 A | 10/2000 | Stiles et al. |
| 6,140,365 A | 10/2000 | Kiy et al. |
| 6,156,561 A | 12/2000 | Kodo et al. |
| 6,174,720 B1 | 1/2001 | Oxley et al. |
| 6,228,332 B1 | 5/2001 | Dunn et al. |
| 6,237,284 B1 | 5/2001 | Erickson |
| 6,258,588 B1 | 7/2001 | Demetropoulos et al. |
| 6,284,453 B1 | 9/2001 | Siano |
| 6,287,852 B1 | 9/2001 | Kondo et al. |
| 6,299,774 B1 | 10/2001 | Ainsworth et al. |
| 6,348,347 B1 | 2/2002 | Hirabayashi et al. |
| 6,391,238 B1 | 5/2002 | Sato et al. |
| 6,477,841 B1 | 11/2002 | Yantovsky |
| 6,492,149 B1 | 12/2002 | Muller-Feuga |
| 6,509,188 B1 | 1/2003 | Trosch et al. |
| 6,524,486 B2 | 2/2003 | Borodyanski et al. |
| 6,571,735 B1 | 6/2003 | Wilkinson |
| 6,579,714 B1 | 6/2003 | Hirabayashi et al. |
| 6,602,703 B2 | 8/2003 | Dutil |
| 6,603,069 B1 | 8/2003 | Muhs et al. |
| 6,633,042 B1 | 10/2003 | Funken et al. |
| 6,648,949 B1 | 11/2003 | Der et al. |
| 6,667,171 B2 | 12/2003 | Bayless et al. |
| 6,673,532 B2 | 1/2004 | Rao |
| 6,673,592 B1 | 1/2004 | Wang et al. |
| 6,709,862 B2 | 3/2004 | Curtis |
| 6,792,336 B1 | 9/2004 | Johnson et al. |
| 6,815,204 B2 | 11/2004 | Muller-Feuga et al. |
| 6,830,699 B2 | 12/2004 | Heidal |
| 6,851,387 B2 | 2/2005 | Untermeyer et al. |
| 6,858,430 B1 | 2/2005 | Reddy et al. |
| 6,887,692 B2 | 5/2005 | Paterek |
| 6,918,354 B2 | 7/2005 | Perriello |
| 6,929,942 B2 | 8/2005 | Moghe et al. |
| 6,936,459 B1 | 8/2005 | Venkatesh et al. |
| 6,989,252 B2 | 1/2006 | Melis et al. |
| 6,991,919 B1 | 1/2006 | Porter et al. |
| 7,001,519 B2 | 2/2006 | Linden et al. |
| 7,022,232 B2 | 4/2006 | Jensen |
| 7,033,823 B2 | 4/2006 | Chang |
| 7,056,725 B1 | 6/2006 | Lu |
| 7,135,308 B1 | 11/2006 | Bush et al. |
| 7,135,332 B2 | 11/2006 | Ouellette |
| 7,153,344 B2 | 12/2006 | Filippi et al. |
| 7,163,811 B2 | 1/2007 | Behrens et al. |
| 7,172,691 B2 | 2/2007 | Dunlop et al. |
| 7,176,017 B2 | 2/2007 | Parent et al. |
| 7,176,024 B2 | 2/2007 | Branson et al. |
| 7,183,074 B2 | 2/2007 | Chen et al. |
| 7,191,597 B2 | 3/2007 | Goldman |
| 7,198,940 B2 | 4/2007 | Vellinger et al. |
| 7,252,979 B2 | 8/2007 | Behrens et al. |
| 7,270,996 B2 | 9/2007 | Cannon et al. |
| 7,279,314 B2 | 10/2007 | Matsuo |
| 7,320,889 B2 | 1/2008 | Kahlert et al. |
| 7,331,178 B2 | 2/2008 | Goldman |
| 7,333,195 B2 | 2/2008 | Kreiβ et al. |
| 7,392,615 B2 | 7/2008 | Lee |
| 7,425,441 B2 | 9/2008 | Broneske et al. |
| 7,435,581 B2 | 10/2008 | West |
| 7,449,313 B2 | 11/2008 | Rush |
| 7,479,226 B2 | 1/2009 | Dunlop et al. |
| 7,507,554 B2 | 3/2009 | Bush et al. |
| 7,507,579 B2 | 3/2009 | Boccazzi et al. |
| 7,510,864 B2 | 3/2009 | Krichevsky et al. |
| 7,514,247 B2 | 4/2009 | Rush |
| 7,531,350 B2 | 5/2009 | Shiau |
| 7,536,827 B2 | 5/2009 | Busch et al. |
| 7,566,551 B2 | 7/2009 | Zhang |
| 7,572,546 B2 | 8/2009 | Karamanev |
| 7,585,898 B2 | 9/2009 | Thothathri |
| 7,618,813 B2 | 11/2009 | Lee et al. |
| 7,632,414 B2 | 12/2009 | Hsu |
| 7,635,586 B2 | 12/2009 | West |
| 7,658,851 B2 | 2/2010 | Nelson et al. |
| 7,662,615 B2 | 2/2010 | Chang et al. |
| 7,662,616 B2 | 2/2010 | Hazlebeck et al. |
| 7,662,617 B2 | 2/2010 | Rush |
| 7,682,821 B2 | 3/2010 | Woods et al. |
| 7,687,161 B2 | 3/2010 | Karamanev |
| 7,687,261 B2 | 3/2010 | Hazlebeck et al. |
| 7,736,508 B2 | 6/2010 | Limcaco |
| 7,750,494 B1 | 7/2010 | Behrens et al. |
| 7,770,322 B2 | 8/2010 | Huntley et al. |
| 7,771,515 B2 | 8/2010 | Champagne et al. |
| 7,890,024 B2 | 2/2011 | Hirayama et al. |
| 7,905,049 B2 | 3/2011 | Erd |
| 7,977,085 B2 | 7/2011 | Rispoli et al. |
| 2002/0034817 A1 | 3/2002 | Henry et al. |
| 2002/0072109 A1 | 6/2002 | Bayless et al. |
| 2002/0130076 A1 | 9/2002 | Merritt |
| 2002/0138454 A1 | 9/2002 | Gruenberg et al. |
| 2003/0044114 A1 | 3/2003 | Pelka |
| 2003/0153059 A1 | 8/2003 | Pilkington et al. |
| 2003/0155090 A1 | 8/2003 | Holmberg et al. |
| 2003/0162273 A1 | 8/2003 | Melis et al. |
| 2003/0228684 A1 | 12/2003 | Burbidge et al. |
| 2004/0077036 A1 | 4/2004 | Thomas et al. |
| 2004/0191755 A1 | 9/2004 | Kemper et al. |
| 2004/0266622 A1 | 12/2004 | Park |
| 2005/0036932 A1 | 2/2005 | Takahashi et al. |
| 2005/0037480 A1 | 2/2005 | Chiueh |
| 2005/0044911 A1 | 3/2005 | Shimose |
| 2005/0064577 A1 | 3/2005 | Berzin |
| 2005/0186671 A1 | 8/2005 | Cannon et al. |
| 2005/0239182 A1 | 10/2005 | Berzin |
| 2005/0244957 A1 | 11/2005 | Stock |
| 2005/0260553 A1 | 11/2005 | Berzin |
| 2006/0019375 A1 | 1/2006 | Seidl et al. |
| 2006/0134598 A1 | 6/2006 | Kenney |
| 2006/0151402 A1 | 7/2006 | Hsu |
| 2006/0216818 A1 | 9/2006 | Amano |
| 2006/0223155 A1 | 10/2006 | Streeter |

(56) References Cited

U.S. PATENT DOCUMENTS

| | | |
|---|---|---|
| 2006/0258000 A1 | 11/2006 | Allen et al. |
| 2006/0275858 A1 | 12/2006 | Saucedo et al. |
| 2006/0281163 A1 | 12/2006 | Diz et al. |
| 2007/0010002 A1 | 1/2007 | Melkonian et al. |
| 2007/0015263 A1 | 1/2007 | Wumpelmann |
| 2007/0042487 A1 | 2/2007 | Cheshire |
| 2007/0048848 A1 | 3/2007 | Sears |
| 2007/0048859 A1 | 3/2007 | Sears |
| 2007/0054351 A1 | 3/2007 | Zhang |
| 2007/0092962 A1 | 4/2007 | Sheppard |
| 2007/0113474 A1 | 5/2007 | Everett et al. |
| 2007/0114186 A1 | 5/2007 | Dart et al. |
| 2007/0157614 A1 | 7/2007 | Goldman |
| 2007/0161095 A1 | 7/2007 | Gurin |
| 2007/0202582 A1 | 8/2007 | Bush et al. |
| 2007/0264708 A1 | 11/2007 | Bayless et al. |
| 2007/0269874 A1 | 11/2007 | Kosourov et al. |
| 2007/0275856 A1 | 11/2007 | Thothathri |
| 2008/0009055 A1 | 1/2008 | Lewnard |
| 2008/0028675 A1 | 2/2008 | Clifford et al. |
| 2008/0044887 A1 | 2/2008 | Maltezos et al. |
| 2008/0050800 A1 | 2/2008 | McKeeman et al. |
| 2008/0052987 A1 | 3/2008 | Busch et al. |
| 2008/0085536 A1 | 4/2008 | Nobles et al. |
| 2008/0086938 A1 | 4/2008 | Hazlebeck et al. |
| 2008/0096267 A1 | 4/2008 | Howard et al. |
| 2008/0113413 A1 | 5/2008 | Nobles et al. |
| 2008/0115500 A1 | 5/2008 | MacAdam et al. |
| 2008/0118964 A1 | 5/2008 | Huntley et al. |
| 2008/0131958 A1 | 6/2008 | Remmereit et al. |
| 2008/0138875 A1 | 6/2008 | Atehortua et al. |
| 2008/0155890 A1 | 7/2008 | Oyler |
| 2008/0160591 A1 | 7/2008 | Willson et al. |
| 2008/0160593 A1 | 7/2008 | Oyler |
| 2008/0160597 A1 | 7/2008 | van der Heiden et al. |
| 2008/0166779 A1 | 7/2008 | Thomas et al. |
| 2008/0176303 A1 | 7/2008 | Massie |
| 2008/0176304 A1 | 7/2008 | Lee |
| 2008/0178739 A1 | 7/2008 | Lewnard et al. |
| 2008/0182325 A1 | 7/2008 | Hobbs et al. |
| 2008/0210632 A1 | 9/2008 | Kruse |
| 2008/0213049 A1 | 9/2008 | Higgins et al. |
| 2008/0213868 A1 | 9/2008 | Fournier |
| 2008/0220486 A1 | 9/2008 | Weiss |
| 2008/0220489 A1 | 9/2008 | Offerman |
| 2008/0220515 A1 | 9/2008 | McCall |
| 2008/0241902 A1 | 10/2008 | Berry et al. |
| 2008/0254056 A1 | 10/2008 | Zhang |
| 2008/0268302 A1 | 10/2008 | McCall |
| 2008/0274494 A1 | 11/2008 | Kertz |
| 2008/0293132 A1 | 11/2008 | Goldman et al. |
| 2008/0299539 A1 | 12/2008 | Lee et al. |
| 2008/0299643 A1 | 12/2008 | Howard et al. |
| 2008/0303348 A1 | 12/2008 | Witters |
| 2008/0305539 A1 | 12/2008 | Hickey et al. |
| 2008/0311646 A1 | 12/2008 | Cong et al. |
| 2008/0318304 A1 | 12/2008 | Burton et al. |
| 2009/0004715 A1 | 1/2009 | Trimbur et al. |
| 2009/0011492 A1 | 1/2009 | Berzin |
| 2009/0017514 A1 | 1/2009 | Datta et al. |
| 2009/0023199 A1 | 1/2009 | Gal |
| 2009/0029445 A1 | 1/2009 | Eckelberry et al. |
| 2009/0035835 A1 | 2/2009 | Slavin |
| 2009/0047722 A1 | 2/2009 | Wilkerson et al. |
| 2009/0047730 A1 | 2/2009 | Higgins et al. |
| 2009/0068715 A1 | 3/2009 | Ogaki et al. |
| 2009/0068727 A1 | 3/2009 | Karr |
| 2009/0075353 A1 | 3/2009 | Ogaki et al. |
| 2009/0077863 A1 | 3/2009 | Oyler |
| 2009/0077864 A1 | 3/2009 | Marker et al. |
| 2009/0081743 A1 | 3/2009 | Hazelbeck et al. |
| 2009/0081744 A1 | 3/2009 | Kastanek |
| 2009/0081748 A1 | 3/2009 | Oyler |
| 2009/0081770 A1 | 3/2009 | Srienc et al. |
| 2009/0104594 A1 | 4/2009 | Webb |
| 2009/0113790 A1 | 5/2009 | Erd |
| 2009/0117647 A1 | 5/2009 | Buddhi Srinivasa et al. |
| 2009/0126265 A1 | 5/2009 | Rasmussen et al. |
| 2009/0130706 A1 | 5/2009 | Berzin et al. |
| 2009/0130747 A1 | 5/2009 | Wen-Teng et al. |
| 2009/0134091 A1 | 5/2009 | Stephens et al. |
| 2009/0137013 A1 | 5/2009 | Schmid et al. |
| 2009/0137025 A1 | 5/2009 | Stephens et al. |
| 2009/0148927 A1 | 6/2009 | Schroeder et al. |
| 2009/0148931 A1 | 6/2009 | Wilkerson et al. |
| 2009/0151240 A1 | 6/2009 | Kayama et al. |
| 2009/0151241 A1 | 6/2009 | Dressler et al. |
| 2009/0155864 A1 | 6/2009 | Bauer et al. |
| 2009/0170184 A1 | 7/2009 | Shepherd et al. |
| 2009/0181438 A1 | 7/2009 | Sayre |
| 2009/0197322 A1 | 8/2009 | Goldman |
| 2009/0203067 A1 | 8/2009 | Eckerle et al. |
| 2009/0203115 A1 | 8/2009 | Busch et al. |
| 2009/0203116 A1 | 8/2009 | Bazaire |
| 2009/0205638 A1 | 8/2009 | Corcoran |
| 2009/0215155 A1 | 8/2009 | Cloud et al. |
| 2009/0221057 A1 | 9/2009 | Kennedy |
| 2009/0227003 A1 | 9/2009 | Blotsky et al. |
| 2009/0227456 A1 | 9/2009 | Hsu |
| 2009/0230040 A1 | 9/2009 | Limcaco |
| 2009/0232861 A1 | 9/2009 | Wright et al. |
| 2009/0233334 A1 | 9/2009 | Hildinger et al. |
| 2009/0249685 A1 | 10/2009 | Flowers et al. |
| 2009/0250401 A1 | 10/2009 | Kotelko et al. |
| 2009/0263889 A1 | 10/2009 | Wumpelmann |
| 2009/0269839 A1 | 10/2009 | Oyler |
| 2009/0275120 A1 | 11/2009 | Koch et al. |
| 2009/0286295 A1 | 11/2009 | Medoff et al. |
| 2009/0286296 A1 | 11/2009 | Hickey et al. |
| 2009/0291485 A1 | 11/2009 | Shigematsu et al. |
| 2009/0294354 A1 | 12/2009 | Theodore et al. |
| 2009/0298159 A1 | 12/2009 | Wu et al. |
| 2009/0305388 A1 | 12/2009 | Dressler et al. |
| 2009/0309515 A1 | 12/2009 | Crabb et al. |
| 2009/0317901 A1 | 12/2009 | Vance |
| 2009/0321349 A1 | 12/2009 | Offerman et al. |
| 2009/0324799 A1 | 12/2009 | Hartman et al. |
| 2009/0325253 A1 | 12/2009 | Ascon et al. |
| 2010/0003717 A1 | 1/2010 | Oyler |
| 2010/0003741 A1 | 1/2010 | Fromson |
| 2010/0005711 A1 | 1/2010 | McNeff |
| 2010/0011778 A1 | 1/2010 | Knight et al. |
| 2010/0018214 A1 | 1/2010 | Halachmi Katchanov |
| 2010/0021968 A1 | 1/2010 | Hu et al. |
| 2010/0028976 A1 | 2/2010 | Hu et al. |
| 2010/0028977 A1 | 2/2010 | Ng et al. |
| 2010/0034050 A1 | 2/2010 | Erb et al. |
| 2010/0035321 A1 | 2/2010 | Wilkerson et al. |
| 2010/0035343 A1 | 2/2010 | Cheng et al. |
| 2010/0043446 A1 | 2/2010 | Shirvanian et al. |
| 2010/0050502 A1 | 3/2010 | Wu et al. |
| 2010/0055765 A1 | 3/2010 | Frank |
| 2010/0062483 A1 | 3/2010 | Beliaev et al. |
| 2010/0068693 A1 | 3/2010 | Tsang et al. |
| 2010/0068779 A1 | 3/2010 | Wells et al. |
| 2010/0068791 A1 | 3/2010 | Merimon et al. |
| 2010/0068801 A1 | 3/2010 | Woods et al. |
| 2010/0071370 A1 | 3/2010 | O'Kane |
| 2010/0077654 A1 | 4/2010 | Wu et al. |
| 2010/0081122 A1 | 4/2010 | Shibuya et al. |
| 2010/0081177 A1 | 4/2010 | Schatz et al. |
| 2010/0081835 A1 | 4/2010 | Wu et al. |
| 2010/0093046 A1 | 4/2010 | Remmereit et al. |
| 2010/0093078 A1 | 4/2010 | Wang et al. |
| 2010/0099151 A1 | 4/2010 | Stroiazzo-Mougin |
| 2010/0099157 A1 | 4/2010 | Salvetzki |
| 2010/0099170 A1 | 4/2010 | Aswani |
| 2010/0101621 A1 | 4/2010 | Xu |
| 2010/0105125 A1 | 4/2010 | Haley |
| 2010/0105126 A1 | 4/2010 | Wright et al. |
| 2010/0105127 A1 | 4/2010 | Ginsburg |
| 2010/0105129 A1 | 4/2010 | Sanchez-Pina et al. |
| 2010/0107487 A1 | 5/2010 | Holland |
| 2010/0112649 A1 | 5/2010 | Willson et al. |

(56) References Cited

U.S. PATENT DOCUMENTS

| | | | |
|---|---|---|---|
| 2010/0112700 A1 | 5/2010 | Shaaltiel et al. |
| 2010/0120134 A1 | 5/2010 | Gal |
| 2010/0139265 A1 | 6/2010 | Stroiazzo |
| 2010/0151558 A1 | 6/2010 | Alianell et al. |
| 2010/0159539 A1 | 6/2010 | Ascon et al. |
| 2010/0159567 A1 | 6/2010 | Kuehnle et al. |
| 2010/0159578 A1 | 6/2010 | Lacaze et al. |
| 2010/0159579 A1 | 6/2010 | Schuring et al. |
| 2010/0162620 A1 | 7/2010 | McCaffrey et al. |
| 2010/0167339 A1 | 7/2010 | Clayton et al. |
| 2010/0167381 A1 | 7/2010 | Woerlee et al. |
| 2010/0170149 A1 | 7/2010 | Keeler et al. |
| 2010/0173355 A1 | 7/2010 | Haase et al. |
| 2010/0173375 A1 | 7/2010 | Oyler |
| 2010/0184177 A1 | 7/2010 | Mitchell |
| 2010/0184194 A1 | 7/2010 | Nagnath |
| 2010/0189806 A1 | 7/2010 | Harper et al. |
| 2010/0190227 A1 | 7/2010 | Dauth et al. |
| 2010/0196995 A1 | 8/2010 | Weissman et al. |
| 2010/0203618 A1 | 8/2010 | Rispoli et al. |
| 2010/0210001 A1 | 8/2010 | Seyfried et al. |
| 2010/0210002 A1 | 8/2010 | McCaffrey et al. |
| 2010/0211812 A1 | 8/2010 | Bullen et al. |
| 2010/0216240 A1 | 8/2010 | Moolman et al. |
| 2010/0227368 A1 | 9/2010 | Steiner |
| 2010/0233786 A1 | 9/2010 | O'Connor |
| 2010/0233787 A1 | 9/2010 | Halachmi Katchanov |
| 2010/0233796 A1 | 9/2010 | Kurihara et al. |
| 2010/0267122 A1 | 10/2010 | Chinnasamy et al. |
| 2010/0273210 A1 | 10/2010 | Reddy |
| 2010/0297739 A1 | 11/2010 | Steiner et al. |
| 2010/0297749 A1 | 11/2010 | Aravanis et al. |
| 2011/0014683 A1 | 1/2011 | Vermaas et al. |
| 2011/0020913 A1 | 1/2011 | Rispoli et al. |
| 2011/0023565 A1 | 2/2011 | Yanik et al. |
| 2011/0027827 A1 | 2/2011 | Chi et al. |
| 2011/0113681 A1 | 5/2011 | Mostertz et al. |
| 2011/0124091 A1 | 5/2011 | Lu et al. |
| 2011/0139409 A1 | 6/2011 | Erd |
| 2011/0159581 A1 | 6/2011 | Zhang et al. |
| 2011/0195473 A1 | 8/2011 | Wilhelm |
| 2011/0195493 A1 | 8/2011 | Stroiazzo-Mougin |
| 2011/0236958 A1 | 9/2011 | Wong |

FOREIGN PATENT DOCUMENTS

| | | |
|---|---|---|
| CA | 2738418 | 11/2011 |
| CA | 2738459 | 11/2011 |
| CA | 2738461 | 11/2011 |
| CA | 2738516 | 11/2011 |
| CN | 2749890 | 1/2006 |
| CN | 101139113 | 3/2008 |
| CN | 101254364 | 9/2008 |
| CN | 201381254 | 1/2010 |
| CN | 101648092 | 2/2010 |
| CN | 101669569 | 3/2010 |
| EP | 2422870 | 2/2012 |
| GB | 2458529 | 9/2009 |
| JP | 3076586 | 4/1991 |
| JP | 4084883 | 3/1992 |
| JP | 4287678 | 10/1992 |
| WO | WO 91/18108 | 11/1991 |
| WO | WO 98/00559 | 1/1998 |
| WO | WO 98/28081 | 7/1998 |
| WO | WO 98/28082 | 7/1998 |
| WO | WO 98/28083 | 7/1998 |
| WO | WO 98/28403 | 7/1998 |
| WO | WO 98/28404 | 7/1998 |
| WO | WO 99/01021 | 1/1999 |
| WO | WO 03/038348 | 5/2003 |
| WO | WO 2005/006838 | 1/2005 |
| WO | WO 2006/020177 | 2/2006 |
| WO | WO 2007/047805 A2 | 4/2007 |
| WO | WO 2007/070452 | 6/2007 |
| WO | WO2007/134141 | 11/2007 |
| WO | WO2008/008262 | 1/2008 |
| WO | WO 2008/028143 | 3/2008 |
| WO | WO 2008/089321 | 7/2008 |
| WO | WO2008/128625 | 10/2008 |
| WO | WO 2008/156795 | 12/2008 |
| WO | WO 2008/156835 | 12/2008 |
| WO | WO 2009/015054 | 1/2009 |
| WO | WO 2009/018498 | 2/2009 |
| WO | WO 2009/094440 | 7/2009 |
| WO | WO 2009/134358 | 11/2009 |
| WO | WO 2009/142765 | 11/2009 |
| WO | WO 2010/002745 | 1/2010 |
| WO | WO 2010/009284 | 1/2010 |
| WO | WO 2010/010554 A1 | 1/2010 |
| WO | WO 2010/011320 | 1/2010 |
| WO | WO 2010/021753 | 2/2010 |
| WO | WO 2010/034023 | 3/2010 |
| WO | WO 2010/094015 A2 | 8/2010 |
| WO | WO 2010/108049 | 9/2010 |
| WO | WO 2011/050578 A1 | 5/2011 |

OTHER PUBLICATIONS

Lee et al. "High density algal photobioreactors using light emitting diodes." *Biotech. BioEng.* [Online] 1994, 44. pp. 1161-1167.

Fernandez et al. "Airlift-driven external-loop tubular photobioreactors for outdoor production of microalgae assessment of design and performance" *Chemical Engineering Science* [Online], 2001, 56, 2721-2732.

Masojidek et al. "A closed solar photobioreactor for cultivation of microalgae under supra-high irradiance basic design and performance" *Journal of Applied Phycology* [Online] 2003, 15, 239-248.

Berenguel et al. "Model predictive control of pH in tubular photobioreactors" *Journal of Process Control*, 2004 14, pp. 377-387.

Degen, et al. "A novel airlift photobioreactor with baffles for improved light utilization through the flashing light effect" *Journal of Biotechnology*, 2001, 92, pp. 89-94.

Putt. "Algae as a Biodiesel Feedstock: A Feasibility Assessment" (Center for Microfibrous Materials Manufacturing, Department of Chemical Engineering, Auburn University, Alabama).

Zebib, "Microalgae Grown in Photobiorecators for Mass Production of Biofuel". Rutger University, Department of Bioenvironmental Engineering, Sep. 2008 http://www.water.rutgers.edu/Educational_Programs/Senior%20Design2008/Algae%20to%20Energy%20Report.pdf.

Wang, et al., "$CO_2$ bio-mitigation using microalgae". Appl. Microbiol. Biotechnol., 2008, vol. 79, pp. 709-718. ISSN: 01757598.

Yang, et al., "Progress in carbon dioxide separation and capture: A review". J.Env. Sci., 2008, vol. 20, pp. 14-27. ISSN: 10010742.

Greenwell, et al., "Placing microalgae on the biofuels priority list: a review of the technological challenges" J. R. Soc. Interface 2010 7, 703-726 first published online Dec. 23, 2009 doi: 10.1098/rsif.2009.0322.

Maeda, et al., "$CO_2$ fixation from the flue gas on coal-fired thermal power plant by microalgae". Energy Convers. Mgmt vol. 36, No. 6-9, pp. 717-720, 1995.

Negoro, et al., "Carbon Dioxide Fixation by Microalgae Photosynthesis Using Actual Flue Gas Discharged from a Boiler". Appl. Biochem. Biotechnol., 1993, vol. 39/40, pp. 643-653. ISSN: 02732289.

Suh, et al., "Photobioreactor Engineering: Design and Performance". Biotechnol. Bioprocess Eng., 2003, vol. 8, No. 6, pp. 313-321. ISSN: 12268372.

O. Pulz "Photobioreactors: production systems for phototrophic microorganisms". Appl. Microbiol. Biotechnol, 2001, vol. 57, pp. 287-293. ISSN: 01757598.

Niels T. Eriksen "The technology of microalgal culturing". Biotechnol Lett., 2008, vol., 30, pp. 1525-1536. ISSN: 01415492.

Carvalho, A.P., et al., "Microalgal Reactors: A Review of Enclosed System Designs and Performances". Biotechnol. Prog., 2006, vol. 22, No. 6, pp. 1490-1506. ISSN: 87567938.

Ishida, M., et al., "$CO_2$ Recovery in a Power Plant with Chemical Looping Combustion". Energy Convers. Mgmt., 1997, vol. 38, Suppl., pp. S187-S192. ISSN: 01968904.

(56) References Cited

OTHER PUBLICATIONS

Cote, R. and Wright, R. "Resource Conservation and Industrial Symbiosis: Strategies for enhancing the environmental sustainability of the Keltic Petrochemical Cluster" Prepared by Eco-Efficiency Centre Dalhousie University, on Mar. 29, 2006, Retrieved on Apr. 19, 2012, Retrieved from the internet: <URL: http://eco-efficiency.management.dal.ca/Files/Keltic Petrochemical Cluster.pdf.

Meridian Planning Consultants Inc., "Bruce Energy Center Discussion Paper, Municipality of Kincardine" Prepared by Meridian Planning Consultants Inc. Jun. 2005, Retrieved on Apr. 19, 2012, Retrieved from the Internet: <URL: http://www.kincardine.net/publicdocs/documents/Bruce%20Energy%20Center%20Discussion%20Paper1.pdf.

Hurst, T., "Canadian Cement Plant Becomes First to Capture CO2 in Algae-A Canadian company called Pond Biofuels is capturing CO2 emissions from a cement plant in algae-algae the company ultimately plans on using to make biofuel." Earth and Industry, Mar. 19, 2010, Retrieved on Apr. 19, 2012, Retrieved from the internet:<URL: http://earthandindustry.com/2010/03/canadian-cement-plant-becomes-first-to-capture-co2-in-algae.

Hamilton, T. "CO2-eating algae turns cement maker green" The Star, Published on Mar. 18, 2010, Retrieved on Apr. 19, 2012, Retrieved from the internet: <URL: http://www.thestar.com/business/article/781426--co2-eating-algae-turns-cement-maker-green.

Janssen M et al., Enclosed outdoor photobireactors: Light regime, photosynthetic efficiency, scale-up, and future prospects. Biotechnology and Bioengineering, vol. 81, Iss. 2, 2003, pp. 193-210.

International Search Report dated Nov. 1, 2011, issued by the ISA/CA, regarding PCT/CA2011/000574.

Written Opinion, mailed Sep. 22, 2011, issued by the ISA/CA, regarding PCT/CA2011/000574.

International Search Report mailed Apr. 19, 2012, issued by the ISA/CA, regarding PCT/CA2011/001367.

Written Opinion mailed Apr. 19, 2012, issued by the ISA/CA, regarding PCT/CA2011/001367.

Stewart, C., et al., "A study of methods of carbon dioxide capture and sequestration—the sustainability of a photosynthetic bioreactor approach", Energy Conversion and Management, 2005, vol. 46, pp. 403-420.

Granum et al., "A photobioreactor with pH control: demonstration by growth of the marine diatom *Skeletonema costatum*", Journal of Plankton Research, vol. 24, No. 6, pp. 557-563 (2002).

Hendershot, R. et al., "Use Oxygen to Improve Combustion and Oxidation", American Institute of Chemical Engineers (AIChE), Chemical Engineering Progress. Jul. 2010. pp. 57-60.

Kunjapur, A. et al., "Photobioreactor Design for Commercial Biofuel Production from Microalgae", Ind. Eng. Chem. Res. 2010. vol. 49, pp. 3516-3526.

Sun, Jian-ming et al., "An Experiment of Enclosed and Constant Culture of Marine Microalgae", Fisheries Sciences, May 2003. vol. 22, No. 3. (including English characterization thereof.).

Aditya M. Kunjapur et al., "Photobioreactor Design for Commercial Biofuel Production from Microalgae", Industrial & Engineering Chemical Research, Mar. 23, 2010, vol. 49, No. 8, pp. 3516-3526.

Supplementary European Search Report for EP Application No. 11782806.1 issued by the European Patent Office on Aug. 1, 2014.

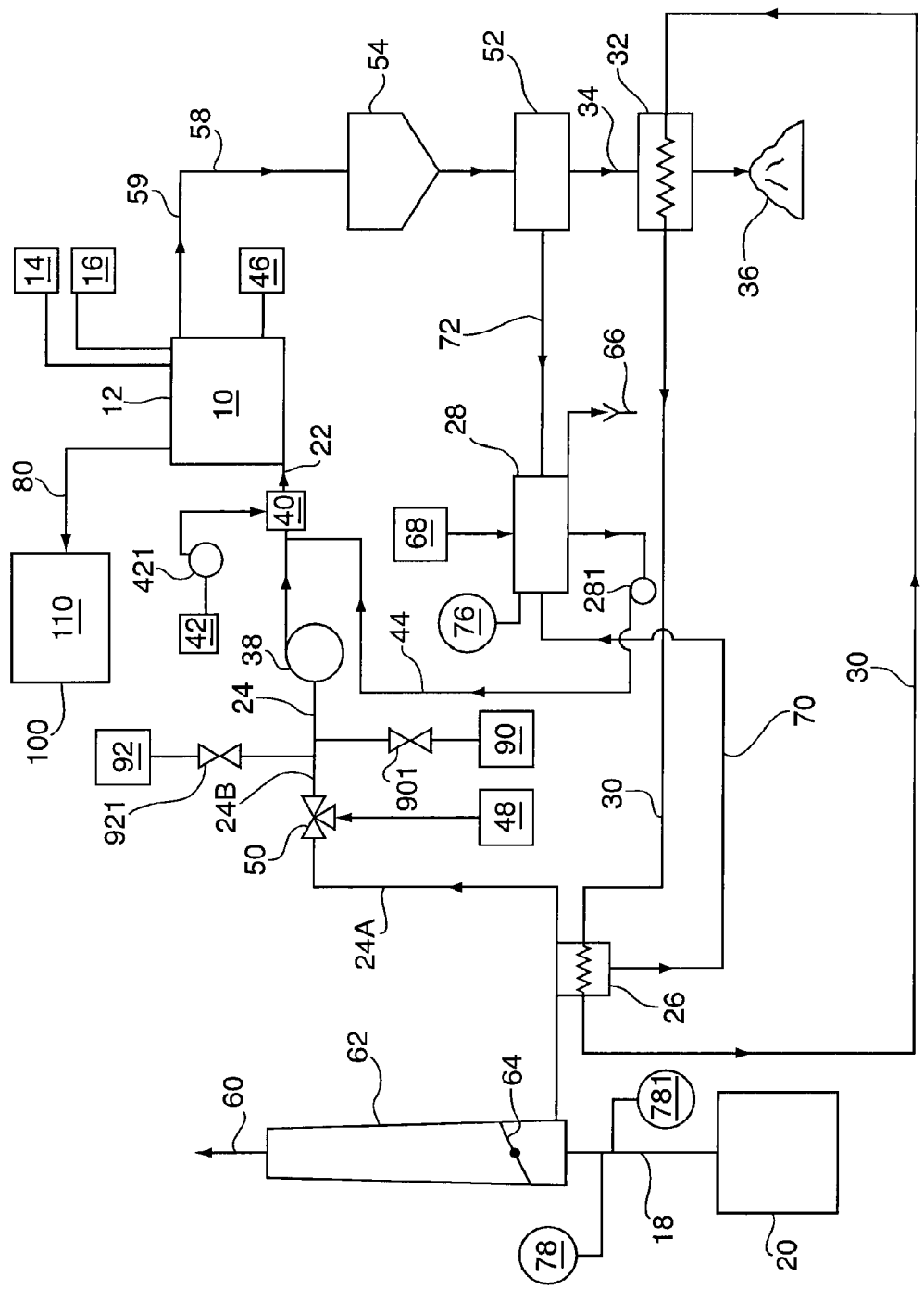

DILUTING EXHAUST GAS BEING SUPPLIED TO BIOREACTOR

FIELD OF THE INVENTION

The present invention relates to a process for growing biomass.

BACKGROUND

The cultivation of phototrophic organisms has been widely practiced for purposes of producing a fuel source. Exhaust gases from industrial processes have also been used to promote the growth of phototrophic organisms by supplying carbon dioxide for consumption by phototrophic organisms during photosynthesis. By providing exhaust gases for such purpose, environmental impact is reduced and, in parallel a potentially useful fuel source is produced. Challenges remain, however, to render this approach more economically attractive for incorporation within existing facilities.

SUMMARY OF THE INVENTION

In one aspect, there is provided a process of growing a phototrophic biomass in a reaction zone. The reaction zone includes an operative reaction mixture. The operative reaction mixture includes the phototrophic biomass disposed in an aqueous medium. Gaseous exhaust material is produced with a gaseous exhaust material producing process, wherein the gaseous exhaust material includes carbon dioxide. Reaction zone feed material is supplied to the reaction zone of a photobioreactor such that any carbon dioxide of the reaction zone feed material is received by the phototrophic biomass so as to provide a carbon dioxide-enriched phototrophic biomass in the aqueous medium. A discharge of the gaseous exhaust material from the gaseous exhaust material producing process is supplied to the reaction zone feed material and defines a gaseous exhaust material reaction zone supply. A supplemental gaseous dilution agent is supplied to the reaction zone feed material. The carbon dioxide concentration of the supplemental gaseous dilution agent is less than the carbon dioxide concentration of the gaseous exhaust material reaction zone supply which is supplied to the reaction zone feed material. The carbon dioxide-enriched phototrophic biomass disposed in the aqueous medium is exposed to photosynthetically active light radiation so as to effect photosynthesis.

BRIEF DESCRIPTION OF THE DRAWINGS

The process of the preferred embodiments of the invention will now be described with the following accompanying drawing:

The FIGURE is a process flow diagram of an embodiment of the process.

DETAILED DESCRIPTION

Referring to the FIGURE, there is provided a process of growing a phototrophic biomass in a reaction zone 10, wherein the reaction zone 10 includes an operative reaction mixture. The operative reaction mixture includes the phototropic biomass disposed in an aqueous medium.

"Phototrophic organism" is an organism capable of phototrophic growth in the aqueous medium upon receiving light energy, such as plant cells and micro-organisms. The phototrophic organism is unicellular or multicellular. In some embodiments, for example, the phototrophic organism is an organism which has been modified artificially or by gene manipulation. In some embodiments, for example, the phototrophic organism is algae. In some embodiments, for example, the algae is microalgae.

"Phototrophic biomass" is at least one phototrophic organism. In some embodiments, for example, the phototrophic biomass includes more than one species of phototrophic organisms.

"Reaction zone 10" defines a space within which the growing of the phototrophic biomass is effected. In some embodiments, for example, the reaction zone 10 is provided in a photobioreactor 12.

"Photobioreactor 12" is any structure, arrangement, land formation or area that provides a suitable environment for the growth of phototrophic biomass. Examples of specific structures which can be used as a photobioreactor 12 by allowing for containment and growth of phototrophic biomass using light energy include, without limitation, tanks, ponds, troughs, ditches, pools, pipes, tubes, canals, and channels. Such photobioreactors may be either open, closed, partially closed, covered, or partially covered. In some embodiments, for example, the photobioreactor 12 is a pond, and the pond is open, in which case the pond is susceptible to uncontrolled receiving of materials and light energy from the immediate environments. In other embodiments, for example, the photobioreactor 12 is a covered pond or a partially covered pond, in which case the receiving of materials from the immediate environment is at least partially interfered with. The photobioreactor 12 includes the reaction zone 10. The photobioreactor 12 is configured to receive a supply of phototrophic reagents (and, in some embodiments other nutrients), and is also configured to effect the recovery or harvesting of biomass which is grown within the reaction zone 10. In this respect, the photobioreactor 12 includes one or more inlets for receiving the supply of phototrophic reagents and other nutrients, and also includes one or more outlets for effecting the recovery or harvesting of biomass which is grown within the reaction zone 10. In some embodiments, for example, one or more of the inlets are configured to be temporarily sealed for periodic or intermittent time intervals. In some embodiments, for example, one or more of the outlets are configured to be temporarily sealed or substantially sealed for periodic or intermittent time intervals. The photobioreactor 12 is configured to contain an operative reaction mixture including an aqueous medium and phototrophic biomass, wherein the aqueous medium is disposed in mass transfer relationship with the phototrophic biomass so as to effect mass transfer of phototrophic reagents from the aqueous medium to the phototrophic biomass. The phototrophic reagents are water and carbon dioxide. The photobioreactor 12 is also configured so as to establish photosynthetically active light radiation (for example, a light of a wavelength between about 400-700 nm, which can be emitted by the sun or another light source) within the photobioreactor 12 for exposing the phototrophic biomass. The exposing of the phototrophic biomass, which includes phototrophic reagents transferred from the aqueous medium, to the photosynthetically active light radiation effects photosynthesis by the phototrophic biomass. In some embodiments, for example, the established light radiation is provided by an artificial light source 14 disposed within the photobioreactor 12. For example, suitable artificial lights sources include submersible fiber optics or light guides, light-emitting diodes ("LEDs"), LED strips and fluorescent lights. Any LED strips known in the art can be adapted for use in the photobioreactor 12. In the case of the submersible LEDs, in some embodiments, for example, energy sources include alternative energy sources, such as wind, photovoltaic cells, fuel cells, etc. to supply electricity to the LEDs. In the case of fiber optics, solar collectors with selective wavelength filters may be used to bring natural light to the photobioreactor 12. Fluorescent lights, external or internal to the photobioreactor 12, can be used as a back-up system. In some embodiments, for example, the established light is derived from a natural light source 16 which has been transmitted from externally of the photobioreactor 12 and through a transmission component. In some embodiments, for example, the transmission component is a portion of a containment structure of the photobioreactor 12 which is at least partially transparent to the photosynthetically active light radiation, and which is configured to provide for transmission of such light to the reaction zone 10 for receiving by the phototrophic biomass. In some embodiments, for example, both natural and artificial lights sources are provided for effecting establishment of the photosynthetically active light radiation within the photobioreactor 12.

"Aqueous medium" is an environment which includes water and sufficient nutrients to facilitate viability and growth of the phototrophic biomass. The nutrients includes dissolved carbon dioxide. In some embodiments, for example, additional nutrients may be included such as one of, or both of, $NO_X$ and $SO_X$. Suitable aqueous media are discussed in detail in: Rogers, L. J. and Gallon J. R. "Biochemistry of the Algae and Cyanobacteria," Clarendon Press Oxford, 1988; Burlew, John S. "Algal Culture: From Laboratory to Pilot Plant." Carnegie Institution of Washington Publication 600. Washington, D.C., 1961 (hereinafter "Burlew 1961"); and Round, F. E. The Biology of the Algae. St Martin's Press, New York, 1965; each of which is incorporated herein by reference). A suitable nutrient composition, known as "Bold's Basal Medium", is described in Bold, H. C. 1949, *The morphology of Chlamydomonas chlamydogama sp. nov. Bull. Torrey Bot. Club.* 76: 101-8 (see also Bischoff, H. W. and Bold, H. C. 1963. *Phycological Studies IV. Some soil algae from Enchanted Rock and related algal species*, Univ. Texas Publ. 6318: 1-95, and Stein, J. (ED.) *Handbook of Phycological Methods, Culture methods and growth measurements*, Cambridge University Press, pp. 7-24).

The process includes producing a gaseous exhaust material 18 with a gaseous exhaust material producing process 20. The gaseous exhaust material includes carbon dioxide. The gaseous exhaust material producing process 20 includes any process which effects production of the gaseous exhaust material. In some embodiments, for example, the gaseous exhaust material producing process 20 is a combustion process being effected in a combustion facility. In some of these embodiments, for example, the combustion process effects combustion of a fossil fuel, such as coal, oil, or natural gas. For example, the combustion facility is any one of a fossil fuel-fired power plant, an industrial incineration facility, an industrial furnace, an industrial heater, or an internal combustion engine. In some embodiments, for example, the combustion facility is a cement kiln.

Reaction zone feed material 22 is supplied to the reaction zone 10 such that any carbon dioxide of the reaction zone feed material 22 is received by the phototrophic biomass so as to provide a carbon dioxide-enriched phototrophic biomass in the aqueous medium. During at least some periods of operation of the process, at least a fraction of the reaction zone feed material 22 is supplied by the gaseous exhaust material 18 which is discharged from the gaseous exhaust material producing process 20. The gaseous exhaust material 18 which is supplied to the reaction zone feed material 22 defines a gaseous exhaust material reaction zone supply 24, and the gaseous exhaust material reaction zone supply 24 includes carbon dioxide. In some embodiments, for example, the gaseous exhaust material 18 includes a carbon dioxide concentration of at least 2 volume % based on the total volume of the gaseous exhaust material 18. In this respect, in some embodiments, for example, the gaseous exhaust material reaction zone supply 24 includes a carbon dioxide concentration of at least 2 volume % based on the total volume of the gaseous exhaust material reaction zone supply 24. In some embodiments, for example, the gaseous exhaust material reaction zone supply 24 also includes one of, or both of, $NO_X$ and $SO_X$.

In some of these embodiments, for example, the gaseous exhaust material reaction zone supply 24 is at least a fraction of the gaseous exhaust material 18 being produced by the gaseous exhaust material producing process 20. In some cases, the gaseous exhaust material reaction zone supply 24 is the gaseous exhaust material 18 being produced by the gaseous exhaust material producing process 20.

In some embodiments, for example, the reaction zone feed material 22 is cooled prior to supply to the reaction zone 10 so that the temperature of the reaction zone feed material 22 aligns with a suitable temperature at which the phototrophic biomass can grow In some embodiments, for example, the gaseous exhaust material reaction zone supply 24 being supplied to the reaction zone material 22 is disposed at a temperature of between 110 degrees Celsius and 150 degrees Celsius. In some embodiments, for example, the temperature of the gaseous exhaust material reaction zone supply 24 is about 132 degrees Celsius. In some embodiments, the temperature at which the gaseous exhaust material reaction zone supply 24 is disposed is much higher than this, and, in some embodiments, such as the gaseous exhaust material reaction zone supply 24 from a steel mill, the temperature is over 500 degrees Celsius. In some embodiments, for example, the reaction zone feed material 22, which has been supplied with the gaseous exhaust material reaction zone supply 24, is cooled to between 20 degrees Celsius and 50 degrees Celsius (for example, about 30 degrees Celsius). Supplying the reaction zone feed material 22 at higher temperatures could hinder growth, or even kill, the phototrophic biomass in the reaction zone 10. In some of these embodiments, in cooling the reaction zone feed material 22, at least a fraction of any water vapour in the reaction zone feed material 22 is condensed in a heat exchanger 26 (such as a condenser) and separated from the reaction zone feed material 22 as an aqueous material 70. In some embodiments, the resulting aqueous material 70 is diverted to a return pond 28 (described below) where it provides supplemental aqueous material for supply to the reaction zone 10. In some embodiments, the condensing effects heat transfer from the reaction zone feed material 22 to a heat transfer medium 30, thereby raising the temperature of the heat transfer medium 30 to produce a heated heat transfer medium 30, and the heat transfer medium 30 is then supplied (for example, flowed) to a dryer 32 (discussed below), and heat transfer is effected from the heated heat transfer medium 30 to an intermediate concentrated biomass product 34 to effect drying of the intermediate concentrated biomass product 34 and thereby effect production of the final biomass product 36. In some embodiments, for example, after being discharged from the dryer 32, the heat transfer medium 30 is recirculated to the heat exchanger 26. Examples of a suitable heat transfer medium 30 include thermal oil and glycol solution.

With respect to the reaction zone feed material 22, the reaction zone feed material 22 is a fluid. In some embodiments, for example, the reaction zone feed material 22 is a gaseous material. In some embodiments, for example, the reaction zone feed material 22 includes gaseous material disposed in liquid material. In some embodiments, for example, the liquid material is an aqueous material. In some of these embodiments, for example, at least a fraction of the gaseous material is dissolved in the liquid material. In some of these embodiments, for example, at least a fraction of the gaseous material is disposed as a gas dispersion in the liquid material. In some of these embodiments, for example, and during at least some periods of operation of the process, the gaseous material of the reaction zone feed material 22 includes carbon dioxide supplied by the gaseous exhaust material reaction zone supply 24. In some of these embodiments, for example, the reaction zone feed material 22 is supplied to the reaction zone 10 as a flow.

In some embodiments, for example, the reaction zone feed material 22 is supplied to the reaction zone 10 as one or more reaction zone feed material flows. For example, each of the one or more reaction zone feed material flows is flowed through a respective reaction zone feed material fluid passage. In some embodiments, for example, a flow of reaction zone feed material 22 is a flow of the gaseous exhaust material reaction zone feed material supply 24.

The supply of the reaction zone feed material 22 to the reaction zone 10 effects agitation of at least a fraction of the phototrophic biomass disposed in the reaction zone 10. In this respect, in some embodiments, for example, the reaction zone feed material 22 is introduced to a lower portion of the reaction zone 10. In some embodiments, for example, the reaction zone feed material 22 is introduced from below the reaction zone 10 so as to effect mixing of the contents of the reaction zone 10. In some of these embodiments, for example, the effected mixing (or agitation) is such that any difference in phototrophic biomass concentration between two points in the reaction zone 10 is less than 20%. In some embodiments, for example, any difference in phototrophic biomass concentration between two points in the reaction zone 10 is less than 10%. In some of these embodiments, for example, the effected mixing is such that a homogeneous suspension is provided in the reaction zone 10. In those embodiments with a photobioreactor 12, for some of these embodiments, for example, the supply of the reaction zone feed material 22 is co-operatively configured with the photobioreactor 12 so as to effect the desired agitation of the at least a fraction of the phototrophic biomass disposed in the reaction zone 10.

With further respect to those embodiments where the supply of the reaction zone feed material 22 to the reaction zone 10 effects agitation of at least a fraction of the phototrophic biomass disposed in the reaction zone 10, in some of these embodiments, for example, the reaction zone feed material 22 flows through a gas injection mechanism, such as a sparger 40, before being introduced to the reaction zone 10. In some of these embodiments, for example, the sparger 40 provides reaction zone feed material 22 to the reaction zone 10 in fine bubbles in order to maximize the interface contact area between the phototrophic biomass and the carbon dioxide (and, in some embodiments, for example, one of, or both of, $SO_X$ and $NO_X$) of the reaction zone feed material 22. This assists the phototrophic biomass in efficiently absorbing the carbon dioxide (and, in some embodiments, or other gaseous components) required for photosynthesis, thereby promoting the optimization of the growth rate of the phototrophic biomass. As well, in some embodiments, for example, the sparger 40 provides reaction zone feed material 22 in larger bubbles that agitate the phototrophic biomass in the reaction zone 10 to promote mixing of the components of the reaction zone 10. An example of a suitable sparger 40 is EDI™ FLEXAIR™ T-Series Tube Diffuser Model 91 X 1003 supplied by Environmental Dynamics Inc of Columbia, Mo. In some embodiments, for example, this sparger 40 is disposed in a photobioreactor 12 having a reaction zone 10 volume of 6000 liters and with an algae concentration of between 0.8 grams per liter and 1.5 grams per liter, and the reaction zone feed material 22 is a gaseous fluid flow supplied at a flowrate of between 10 cubic feet per minute and 20 cubic feet per minute, and at a pressure of about 68 inches of water.

With respect to the sparger 40, in some embodiments, for example, the sparger 40 is designed to consider the fluid head of the reaction zone 10, so that the supplying of the reaction zone feed material 22 to the reaction zone 10 is effected in such a way as to promote the optimization of carbon dioxide absorption by the phototrophic biomass. In this respect, bubble sizes are regulated so that they are fine enough to promote optimal carbon dioxide absorption by the phototrophic biomass from the reaction zone feed material. Concomitantly, the bubble sizes are large enough so that at least a fraction of the bubbles rise through the entire height of the reaction zone 10, while mitigating against the reaction zone feed material 22 "bubbling through" the reaction zone 10 and being released without being absorbed by the phototrophic biomass. To promote the realization of an optimal bubble size, in some embodiments, the pressure of the reaction zone feed material 22 is controlled using a pressure regulator upstream of the sparger 40.

With respect to those embodiments where the reaction zone 10 is disposed in a photobioreactor 12, in some of these embodiments, for example, the sparger 40 is disposed externally of the photobioreactor 12. In other embodiments, for example, the sparger 40 is disposed within the photobioreactor 12. In some of these embodiments, for example, the sparger 40 extends from a lower portion of the photobioreactor 12 (and within the photobioreactor 12).

In some embodiments, for example, the reaction zone feed material 22 is supplied at a pressure which effects flow of the reaction zone feed material 22 through at least a seventy (70) inch vertical extent of the aqueous medium. In some of these embodiments, for example, the supplying of the reaction zone feed material 22 is effected while the gaseous exhaust material 18 is being produced by the gaseous exhaust material producing process 20. In some embodiments, for example, the supplying of the reaction zone feed material 22 to the reaction zone 10 is effected while the gaseous exhaust material reaction zone supply 24 is being supplied to the reaction zone feed material 22. In some of these embodiments, the exposing of the carbon dioxide-enriched phototrophic biomass disposed in the aqueous medium to photosynthetically active light radiation is effected while the supplying of the reaction zone feed material 22 is being effected. In some of these embodiments, for example, the reaction zone feed material 22 is a gaseous flow. In some of these embodiments, for example, the pressure of the flow of the reaction zone feed material 22 is increased before being supplied to the reaction zone 10. In some embodiments, for example, the pressure increase is at least partially effected by a prime mover 38. For those embodiments where the pressure increase is at least partially effected by the prime mover 38, examples of a suitable prime mover 38 include a blower, a compressor, a pump (for embodiments where the reaction zone feed material 22 includes liquid material), and an air pump. In other embodiments, for example, the pressure increase is effected by a jet pump or eductor. With respect to such embodiments, where the pressure increase is effected by a jet pump or eductor, in some of these embodiments, for example, the gaseous exhaust material reaction zone supply 24 is supplied to the jet pump or eductor and pressure energy is transferred to the gaseous exhaust material reaction zone from another flowing fluid using the venturi effect to effect the pressure increase in the reaction zone feed material 24. In some of these embodiments, for example, the another flowing fluid includes liquid material and, in this respect, the resulting flow of reaction zone feed material 24 includes a combination of liquid and gaseous material. The pressure increase is designed to overcome the fluid head within the reaction zone 10.

In some embodiments, for example, the photobioreactor 12, or plurality of photobioreactors 12, are configured so as to optimize carbon dioxide absorption by the phototrophic biomass and reduce energy requirements. In this respect, the photobioreactor(s) is, or are, configured to provide increased residence time of the carbon dioxide within the reaction zone 10. As well, movement of the carbon dioxide over horizontal distances is minimized, so as to reduce energy consumption. To this end, the photobioreactor 12 is, or are, relatively taller, and provide a reduced footprint, so as to increase carbon dioxide residence time while conserving energy.

In some embodiments, for example, a nutrient supply 42 is supplied to the reaction zone 10. In some embodiments, for example, the nutrient supply 42 is effected by a pump, such as a dosing pump. In other embodiments, for example, the nutrient supply 42 is supplied manually to the reaction zone 10. Nutrients within the reaction zone 10 are processed or consumed by the phototrophic biomass, and it is desirable, in some circumstances, to replenish the processed or consumed nutrients. A suitable nutrient composition is "Bold's Basal Medium", and this is described in Bold, H. C. 1949, *The morphology of Chlamydomonas chlamydogama sp. nov. Bull. Torrey Bot. Club.* 76: 101-8 (see also Bischoff, H. W. and Bold, H. C. 1963. *Phycological Studies IV. Some soil algae from Enchanted Rock and related algal species*, Univ. Texas Publ. 6318: 1-95, and Stein, J. (ED.) *Handbook of Phycological Methods, Culture methods and growth measurements*, Cambridge University Press, pp. 7-24).

In some of these embodiments, the rate of supply of the nutrient supply 42 to the reaction zone 10 is controlled to align with a desired rate of growth of the phototrophic biomass in the reaction zone 10. In some embodiments, for example, regulation of nutrient addition is monitored by measuring any combination of pH, $NO_3$ concentration, and conductivity in the reaction zone 10.

In some embodiments, for example, a supplemental aqueous material supply 44 is supplied to the reaction zone 10 of the photobioreactor 12. Supply of the supplemental aqueous material supply 44 is effected to the reaction zone 10 so as to replenish the contents of the photobioreactor 12. The supplemental aqueous material supply 44 includes at least one of: (a) aqueous material which has been condensed from the reaction zone feed material 22 while the reaction zone feed material 22 is cooled before being supplied to the reaction zone 10, and (b) aqueous material which has been separated from the discharged biomass product 59.

In some embodiments, for example, the supplemental aqueous material supply 44 is supplied by a pump. In some of these embodiments, for example, the supplemental aqueous material supply 44 is continuously supplied to the reaction zone 10 to effect harvesting of the biomass by overflow of the discharged biomass product 59.

In this respect, in some of these embodiments, for example, the process further includes discharging the biomass product 59 from the photobioreactor 12, wherein the product includes at least a fraction of the contents of the reaction zone 10 of the photobioreactor 12. In some of these embodiments, for example, the discharging of the biomass product 59 is effected by an overflow of the at least a fraction of the contents of the reaction zone 10 of the photobioreactor 12. When the upper level of the contents of the reaction zone 10 within the photobioreactor 12 becomes disposed below a predetermined minimum level, the supplying of, or an increase to the molar rate of supply, of the supplemental aqueous material supply 44 (which has been recovered from the process) is effected to the reaction zone 10. In some embodiments, for example, the recovered aqueous material is water.

In some embodiments, for example, at least a fraction of the supplemental aqueous material supply 44 is supplied from a return pond 28, which is further described below. At least a fraction of aqueous material which is discharged from the process is recovered and supplied to the return pond 28 to provide supplemental aqueous material in the return pond 28.

In some embodiments, for example, the nutrient supply 42 and the supplemental aqueous material supply 44 are supplied to the reaction zone 10 as a portion of the reaction zone feed material 22. In this respect, in some of these embodiments, the nutrient supply 42 and the supplemental aqueous material supply 44 are supplied to the reaction zone feed material 22 in the sparger 40 before being supplied to the reaction zone 10. In those embodiments where the reaction zone 10 is disposed in the photobioreactor 12, in some of these embodiments, for example, the sparger 40 is disposed externally of the photobioreactor 12. In some embodiments, it is desirable to mix the gaseous exhaust material reaction zone supply 24 with the nutrient supply 42 and the supplemental aqueous material supply 44 within the sparger 40, as this effects better mixing of these components versus separate supplies of the reaction zone feed material 22, the nutrient supply 42, and the supplemental aqueous material supply 44. On the other hand, the rate of supply of the reaction zone feed material 22 to the reaction zone 10 is limited by virtue of saturation limits of gaseous material of the reaction zone feed material 22 in the combined mixture. Because of this trade-off, such embodiments are more suitable when response time required for providing a modulated supply of carbon dioxide to the reaction zone 10 is not relatively immediate, and this depends on the biological requirements of the phototrophic organisms being used.

In some of the embodiments, for example, at least a fraction of the nutrient supply 42 is mixed with the supplemental aqueous material in the return pond 28 to provide a nutrient-enriched supplemental aqueous material supply 44, and the nutrient-enriched supplemental aqueous material supply 44 is supplied directly to the reaction zone 10 or is mixed with the reaction zone feed material 22 in the sparger 40. In some embodiments, for example, the direct or indirect supply of the nutrient-enriched supplemental aqueous material supply is effected by a pump.

The carbon dioxide-enriched phototrophic biomass disposed in the aqueous medium is exposed to photosynthetically active light radiation so as to effect photosynthesis. In some embodiments, for example, the light radiation is characterized by a wavelength of between 400-700 nm. In some embodiments, for example, the light radiation is in the form of natural sunlight. In some embodiments, for example, the light radiation is provided by an artificial light source 14. In some embodiments, for example, light radiation provided is both of natural sunlight and artificial light.

In some embodiments, for example, the intensity of the provided light is controlled so as to align with the desired growth rate of the phototrophic biomass in the reaction zone 10. In some embodiments, regulation of the intensity of the provided light is based on measurements of the growth rate of the phototrophic biomass in the reaction zone 10. In some embodiments, regulation of the intensity of the provided light is based on the molar rate of supply of carbon dioxide to the reaction zone feed material 22.

In some embodiments, for example, the light is provided at pre-determined wavelengths, depending on the conditions of the reaction zone 10. Having said that, generally, the light is provided in a blue light source to red light source ratio of 1:4. This ratio varies depending on the phototrophic organism being used. As well, this ratio may vary when attempting to simulate daily cycles. For example, to simulate dawn or dusk, more red light is provided, and to simulate mid-day condition, more blue light is provided. Further, this ratio may be varied to simulate artificial recovery cycles by providing more blue light.

It has been found that blue light stimulates algae cells to rebuild internal structures that may become damaged after a period of significant growth, while red light promotes algae growth. Also, it has been found that omitting green light from the spectrum allows algae to continue growing in the reaction zone 10 even beyond what has previously been identified as its "saturation point" in water, so long as sufficient carbon dioxide and, in some embodiments, other nutrients, are supplied.

With respect to artificial light sources, for example, suitable artificial light source 14 include submersible fiber optics, light-emitting diodes, LED strips and fluorescent lights. Any LED strips known in the art can be adapted for use in the process. In the case of the submersible LEDs, the design includes the use of solar powered batteries to supply the electricity. In the case of the submersible LEDs, in some embodiments, for example, energy sources include alternative energy sources, such as wind, photovoltaic cells, fuel cells, etc. to supply electricity to the LEDs. In the case of fiber optics, solar collectors with selective wavelength filters may be used to bring natural light to the photobioreactor 12. In the case of fiber optics, solar collectors with UV filters may be used to bring natural light to the reactor. Fluorescent lights can be used as a back-up system.

With respect to those embodiments where the reaction zone 10 is disposed in a photobioreactor 12 which includes a tank, in some of these embodiments, for example, the light energy is provided from a combination of sources, as follows. Natural light source 16 in the form of solar light is captured though solar collectors and filtered with custom mirrors that effect the provision of light of desired wavelengths to the reaction zone 10. The filtered light from the solar collectors is then transmitted to light tubes in the photobioreactor 12, where it becomes dispersed within the reaction zone 10. In addition to solar light, the light tubes in the photobioreactor 12 contains high power LED arrays that can provide light at specific wavelengths to either complement solar light, as necessary, or to provide all of the necessary light to the reaction zone 10 during periods of darkness (for example, at night). In some embodiments, for example, a transparent heat transfer medium (such as a glycol solution) is circulated through light guides within the photobioreactor 12 so as to regulate the temperature in the light tubes and, in some circumstances, provide for the controlled dissipation of heat from the light tubes and into the reaction zone 10. In some embodiments, for example, the LED power requirements can be predicted and, therefore, controlled, based on trends observed with respect to the gaseous exhaust material 18, as these observed trends assist in predicting future growth rate of the phototrophic biomass.

In some embodiments, for example, the growth rate of the phototrophic biomass is dictated by the available gaseous exhaust material reaction zone supply 24. In turn, this defines the nutrient, water, and light intensity requirements to maximize phototrophic biomass growth rate. In some embodiments, for example, a controller, e.g. a computer-implemented system, is provided to be used to monitor and control the operation of the various components of the process disclosed herein, including lights, valves, sensors, blowers, fans, dampers, pumps, etc.

In some circumstances, it is desirable to grow phototrophic biomass using carbon dioxide of the gaseous exhaust material 18 being discharged from the gaseous exhaust material producing process 20, but the carbon dioxide concentration in the discharged gaseous exhaust material 18 is excessive for effecting optimal growth of the phototrophic biomass. In this respect, the phototrophic biomass responds adversely when exposed to the reaction zone feed material 22 which is supplied by the gaseous exhaust material reaction zone supply 24 of the gaseous exhaust material 18, by virtue of the carbon dioxide concentration of the reaction zone feed material 22, which is attributable to the carbon dioxide concentration of the gaseous exhaust reaction zone supply 24.

In this respect, when at least a fraction of the reaction zone feed material 22 is supplied by a gaseous exhaust material reaction zone supply 24, the process further includes, supplying the reaction zone feed material 22 with a supplemental gaseous dilution agent 90, wherein the carbon dioxide concentration of the supplemental gaseous dilution agent 90 is less than the carbon dioxide concentration of the gaseous exhaust material reaction zone supply 24 which is supplied to the reaction zone feed material 22. In some of these embodiments, for example, the supplying of the supplemental gaseous dilution agent 90 to the reaction zone feed material 22 provides a carbon dioxide concentration in the reaction zone feed material 22 being supplied to the reaction zone 10 which is below a predetermined maximum carbon dioxide concentration value. In some of these embodiments, for example, the supplying of the supplemental gaseous dilution agent 90 to the reaction zone feed material 22 effects dilution of the reaction zone feed material 22 with respect to carbon dioxide concentration (i.e. effects reduction of carbon dioxide concentration in the reaction zone feed material 22).

In some of these embodiments, for example, the reaction zone feed material 22 includes an upstream reaction zone feed material 24A and a downstream reaction zone feed material 24B, wherein the downstream reaction zone feed material 24B is downstream of the upstream reaction zone feed material 24A relative to the reaction zone 10. The supplemental gaseous dilution agent 90 is admixed with the upstream reaction zone feed material 24A to provide the downstream reaction zone feed material 24B such that the concentration of carbon dioxide in the downstream reaction zone feed material 24B is less than the concentration of carbon dioxide in the upstream reaction zone feed material 24A. In some embodiments, for example, the upstream reaction zone feed material 24A is a gaseous material.

In some embodiments, for example, the supplying of the supplemental gaseous dilution agent 90 to the reaction zone feed material 22 is effected in response to sensing of a carbon dioxide concentration in the gaseous exhaust material 18 being discharged from the carbon dioxide producing process 20 which is greater than a predetermined maximum carbon dioxide concentration value. In some embodiments, when a carbon dioxide concentration of the gaseous exhaust material 18 is sensed which is greater than a predetermined maximum carbon dioxide concentration value, a signal is transmitted to the controller, and the controller actuates opening of a control valve 901 which effects supply of the supplemental gaseous dilution agent 90 to the reaction zone feed material 22.

In some of these embodiments, for example, the supplying of the reaction zone feed material 22 with a supplemental gaseous dilution agent 90 is effected while the gaseous exhaust material 18 is being produced by the gaseous exhaust material producing process 20. In some of these embodiments, for example, the supplying of the reaction zone feed material 22 with a supplemental gaseous dilution agent 90 is effected while the gaseous exhaust material reaction zone supply 24 is being supplied to the reaction zone feed material 22. In some embodiments, for example, the supplying of the reaction zone feed material 22 with a supplemental gaseous dilution agent 90 is effected while the reaction zone feed material 22 is being supplied to the reaction zone 10. In some of these embodiments, the exposing of the carbon dioxide-enriched phototrophic biomass disposed in the aqueous medium to photosynthetically active light radiation is effected while the supplying of the reaction zone feed material 22 with a supplemental gaseous dilution agent 90 is being effected.

In some embodiments, the reaction zone feed material 22 is supplied to the reaction zone 10 as a flow. In some embodiments, for example, the supplemental gaseous dilution agent 90 is gaseous material. In some embodiments, for example, the supplemental gaseous dilution agent 90 includes air. In some embodiments, for example, the supplemental gaseous dilution agent 90 is being supplied to the reaction zone feed material 22 as a flow. In some embodiments, for example, the supplemental gaseous dilution agent 90 is a gaseous material and is supplied as a flow for admixing with the upstream reaction zone material supply 24A.

In some embodiments, for example, when at least a fraction of the reaction zone feed material 22 is supplied by a gaseous exhaust material reaction zone supply 24, and when an indication of a change in the molar rate of supply of carbon dioxide in the gaseous exhaust material reaction zone supply 24 (i.e. supply to the reaction zone feed material 22) is sensed, modulation of at least one input to the reaction zone 10 is effected. The modulating of at least one input includes at least one of: (a) effecting or eliminating supply of, or modulating the intensity of, the photosynthetically active light radiation to which at least a fraction of the carbon dioxide-enriched phototrophic biomass is exposed, and (b) effecting, modulating, or eliminating the molar rate of supply, or commencing supply, of a nutrient supply 42 to the reaction zone 10. In some embodiments, for example, the modulating of at least one input is effected while the gaseous exhaust material 18 is being produced by the gaseous exhaust material producing process 20. In some embodiments, for example, the modulating of at least one input is effected while the gaseous exhaust material reaction zone supply 24 is being supplied to the reaction zone feed material 22. In some embodiments, for example, the modulating of at least one input is effected while the reaction zone feed material 22 is being supplied to the reaction zone 10. In some of these embodiments, the exposing of the carbon dioxide-enriched phototrophic biomass disposed in the aqueous medium to photosynthetically active light radiation is effected while the modulating of at least one input is being effected.

In some embodiments, for example, the effecting or the eliminating of the supply of, or modulating the intensity of, the photosynthetically active light radiation is effected by the controller. To increase or decrease light intensity, the controller changes the power output from the power supply, and this can be effected by controlling either one of voltage or current. As well, in some embodiments, for example, the effecting, modulating, or eliminating the molar rate of supply, or commencing supply, of a nutrient supply 42 is also effected by the controller. To increase or decrease nutrient supply 42, the controller can control a dosing pump 421 to provide a desired flow rate of the nutrient supply 42.

In some of these embodiments, for example, when at least a fraction of the reaction zone feed material 22 is supplied by a gaseous exhaust material reaction zone supply 24, and when an indication of an increase in the molar rate of supply of carbon dioxide in the gaseous exhaust material reaction zone supply 24 (i.e. supply to the reaction zone feed material 22) is sensed, the modulating of at least one input includes effecting at least one of: (a) an increase in the intensity of the photosynthetically active light radiation to which at least a fraction of the carbon dioxide-enriched phototrophic biomass is exposed, and (b) an increase in the molar rate of supply, or commencement of supply, of a nutrient supply 42 to the reaction zone 10. In some embodiments, for example, the increase in the intensity of the photosynthetically active light radiation is proportional to the increase in the molar rate of supply of carbon dioxide in the gaseous exhaust material reaction zone supply 24.

In some embodiments, for example, the gaseous exhaust material reaction zone supply 24 is supplied as a flow to the reaction zone feed material 22, and the indication of an increase in the molar rate of supply of carbon dioxide in the gaseous exhaust material reaction zone supply 24 which is sensed is an increase in molar flowrate of the gaseous exhaust material 18 being produced by the gaseous exhaust material producing process 20. In this respect, in some embodiments, for example, a flow sensor 78 is provided, and upon sensing an increase in the molar flow rate of the gaseous exhaust material 18 being produced, the flow sensor 78 transmits a signal to the controller, and the controller effects at least one of: (a) an increase in the intensity of the photosynthetically active light radiation to which at least a fraction of the carbon dioxide-enriched phototrophic biomass is exposed, and (b) an increase in the molar rate of supply, or commencement of supply, of a nutrient supply 42 to the reaction zone 10.

In some embodiments, for example, the indication of an increase in the molar rate of supply of carbon dioxide in the gaseous exhaust material reaction zone supply 24 which is sensed is an increase in carbon dioxide concentration of the discharged gaseous effluent 18. In this respect, in some embodiments, for example, a carbon dioxide sensor 781 is provided, and upon sensing an increase in the carbon dioxide concentration of the gaseous exhaust material 18 being produced, the carbon dioxide sensor 781 transmits a signal to the controller, and the controller effects at least one of: (a) an increase in the intensity of the photosynthetically active light radiation to which at least a fraction of the carbon dioxide-enriched phototrophic biomass is exposed, and (b) an increase in the molar rate of supply, or commencement of supply, of a nutrient supply 42 to the reaction zone 10.

In some embodiments, for example, at least one of: (a) an indication of an increase in the molar flow rate of the gaseous exhaust material 18 being produced, and (b) an indication of an increase in the carbon dioxide concentration of the gaseous exhaust material 18 being produced, is a signal of an impending increase in the rate of molar supply of carbon dioxide to the reaction zone feed material 22. Because an increase in the rate of molar supply of carbon dioxide to the reaction zone feed material 22 is impending, the molar rate of supply of at least one condition for growth (i.e. increased rate of supply of carbon dioxide) of the phototrophic biomass is increased, and the rates of supply of other inputs, relevant to such growth, are correspondingly increased, in anticipation of growth of the phototrophic biomass in the reaction zone 10.

In some embodiments, for example, when at least a fraction of the reaction zone feed material 22 is supplied by a gaseous exhaust material reaction zone supply 24, and when an indication of a decrease in the molar rate of supply of carbon dioxide in the gaseous exhaust material reaction zone supply 24 (i.e. supply to the reaction zone feed material 22) is sensed, the modulating of at least one input includes effecting at least one of: (a) a decrease in the intensity of the photosynthetically active light radiation to which at least a fraction of the carbon dioxide-enriched phototrophic biomass is exposed, and (b) a decrease in the molar rate of supply, or elimination of supply, of a nutrient supply 42 to the reaction zone 10. In some embodiments, for example, the decrease in the intensity of the photosynthetically active light radiation is proportional to the decrease in the molar rate of supply of carbon dioxide in the gaseous exhaust material reaction zone supply 24.

In some embodiments, for example, when the gaseous exhaust material reaction zone supply 24 is supplied as a flow to the reaction zone feed material 22, the indication of a decrease in the molar rate of supply of carbon dioxide in the gaseous exhaust material reaction zone supply 24 which is sensed is a decrease in flow of the gaseous exhaust material 18 being produced by the gaseous exhaust material producing process 20. In this respect, in some embodiments, for example, a flow sensor 78 is provided, and upon sensing a decrease in the flow, the flow sensor 78 transmits a signal to the controller, and the controller effects at least one of: (a) a decrease in the intensity of the photosynthetically active light radiation to which at least a fraction of the carbon dioxide-enriched phototrophic biomass is exposed, and (b) a decrease in the molar rate of supply, or elimination of supply, of a nutrient supply 42 to the reaction zone 10.

In some embodiments, for example, the indication of a decrease in the molar rate of supply of carbon dioxide in the gaseous exhaust material reaction zone supply 24 which is sensed is a decrease in carbon dioxide concentration of the discharged gaseous effluent 18. In this respect, in some embodiments, for example, a carbon dioxide sensor 781 is provided, and upon sensing a decrease in the carbon dioxide concentration of the gaseous exhaust material 18 being produced, the carbon dioxide sensor 781 transmits a signal to the controller, and the controller effects at least one of: (a) a decrease in the intensity of the photosynthetically active light radiation to which at least a fraction of the carbon dioxide-enriched phototrophic biomass is exposed, and (b) a decrease in the molar rate of supply, or commencement of supply, of a nutrient supply 42 to the reaction zone 10.

In some embodiments, for example, at least one of: (a) an indication of a decrease in the molar flow rate of the gaseous exhaust material 18 being produced, and (b) an indication of a decrease in the carbon dioxide concentration of the gaseous exhaust material 18 being produced, is a signal of an impending decrease in the rate of molar supply of carbon dioxide to the reaction zone feed material 22. Because a decrease in the rate of molar supply of carbon dioxide to reaction zone feed material 22 is impending, the rate of supply of other inputs, which would otherwise be relevant to phototrophic biomass growth, are correspondingly reduced to conserve such inputs. In these circumstances, the molar rate of supply of carbon dioxide to the reaction zone feed material 22 is still sufficient so that phototrophic biomass growth continues, albeit at a reduced rate, and efficient growth of the phototrophic biomass continues to be promoted, albeit at a reduced rate.

On the other hand, in some embodiments, the indication of a decrease in the molar rate of supply of carbon dioxide in the gaseous exhaust material reaction zone supply which is sensed is sufficiently significant such that there is a risk of conditions being created in the reaction zone 10 which are adverse to growth of the phototrophic biomass or, in the extreme, which may result in the death of at least a fraction of the phototrophic biomass. However, because it is believed that the decrease in the molar rate of supply of carbon dioxide in the gaseous exhaust material reaction zone supply 24 is of a temporary nature, it is desirable to take steps to preserve the phototrophic biomass in the reaction zone 10 until the molar rate of supply of carbon dioxide in the gaseous exhaust material reaction zone supply 24 returns to levels which are capable of sustaining meaningful growth of the phototrophic biomass in the reaction zone 10.

In this respect, in some embodiments, when at least a fraction of the reaction zone feed material 22 is supplied by a gaseous exhaust material reaction zone supply 24, and when an indication of a decrease in the molar rate of supply of carbon dioxide in the gaseous exhaust material reaction zone supply 24 (i.e. supply the reaction zone feed material 22) is sensed, either the molar rate of supply of a supplemental carbon dioxide supply 92 to the reaction zone feed material 22 is increased, or supply of the supplemental carbon dioxide supply to the reaction zone feed material 22 is initiated 92. In some of these embodiments, for example, the increasing of the molar rate of supply, or the initiation of supply, of a supplemental carbon dioxide supply 92 to the reaction zone feed material 22 is effected while the gaseous exhaust material 18 is being produced by the gaseous exhaust material producing process 20. In some of these embodiments, for example, the increasing of the molar rate of supply, or the initiation of supply, of a supplemental carbon dioxide supply 92 to the reaction zone feed material 22 is effected while the gaseous exhaust material reaction zone supply 24 is being supplied to the reaction zone feed material 22. In some embodiments, for example, the increasing of the molar rate of supply, or the initiation of supply, of a supplemental carbon dioxide supply 92 to the reaction zone feed material 22 is effected while the reaction zone feed material 22 is being supplied to the reaction zone 10. In some of these embodiments, the exposing of the carbon dioxide-enriched phototrophic biomass disposed in the aqueous medium to photosynthetically active light radiation is effected while the increasing of the molar rate of supply, or the initiation of supply, of the supplemental carbon dioxide supply 92 to the reaction zone feed material 22 is being effected.

In those embodiments where the increasing of the molar rate of supply, or the initiation of supply, of a supplemental carbon dioxide supply 92 to the reaction zone 10 is effected in response to an indication of a decrease in the molar rate of supply of carbon dioxide in the gaseous exhaust material reaction zone supply 24, in some of these embodiments, for example, when the gaseous exhaust material reaction zone supply 24 is supplied as a flow to the reaction zone feed material 22, the indication of a decrease in the molar rate of supply of carbon dioxide in the gaseous exhaust material reaction zone supply 24 which is sensed is a decrease in flow of the gaseous exhaust material 18 being produced by the gaseous exhaust material producing process 20. In this respect, in some of these embodiments, for example, a flow sensor 78 is provided, and upon sensing the decrease in the flow of the gaseous exhaust material 18 being produced by the gaseous exhaust material producing process 22, the flow sensor 78 transmits a signal to the controller, and the controller actuates the opening of a flow control element, such as a valve 921, to effect supply of the supplemental carbon dioxide supply 92 to the reaction zone feed material 22, or to effect increasing of the molar rate of supply of the supplemental carbon dioxide supply to the reaction zone feed material 22.

In those embodiments where the increasing of the molar rate of supply, or the initiation of supply, of a supplemental carbon dioxide supply 92 to the reaction zone 10 is effected in response to an indication of a decrease in the molar rate of supply of carbon dioxide in the gaseous exhaust material reaction zone supply 24, in some of these embodiments, for example, the indication of a decrease in the molar rate of supply of carbon dioxide in the gaseous exhaust material reaction zone supply 24 which is sensed is a decrease in molar concentration of carbon dioxide within the gaseous exhaust material 18 being produced by the gaseous exhaust material producing process 20. In this respect, in some embodiments, for example, a carbon dioxide sensor 781 is provided, and upon sensing a decrease in the carbon dioxide concentration of the gaseous exhaust material 18 being produced, the carbon dioxide sensor 781 transmits a signal to the controller, and the controller actuates the opening of a flow control element, such as a valve 921, to effect supply of the supplemental carbon dioxide supply to the reaction zone feed material 22, or to effect increasing of the molar rate of supply of the supplemental carbon dioxide supply to the reaction zone feed material 22.

In some embodiments, for example, a discharge of the gaseous exhaust material 18 from the gaseous exhaust material producing process 20 is modulated based on sensing of at least one reaction zone parameter. In some embodiments, for example, the sensing of at least one of the at least one reaction zone parameter is effected in the reaction zone 10. The modulating of the discharge of the gaseous exhaust material 18 includes modulating of a supply of the discharged gaseous exhaust material 18 to the reaction zone feed material 22. As described above, the supply of the discharged gaseous exhaust material 18 to the reaction zone feed material 22 defines the gaseous exhaust material reaction zone supply 24. The gaseous exhaust material reaction zone supply 24 includes carbon dioxide. In some embodiments, for example, the discharged gaseous exhaust material 18 is provided in the form of a gaseous flow. In some embodiments, for example, the gaseous exhaust material reaction zone supply 24 is provided in the form of a gaseous flow.

In some embodiments, for example, the modulating of the discharge of the gaseous exhaust material 18 further includes modulating of a supply of the discharged gaseous exhaust material 18 to another unit operation. The supply of the discharged gaseous exhaust material 18 to another unit operation defines a bypass gaseous exhaust material 60. The bypass gaseous exhaust material 60 includes carbon dioxide. The another unit operation converts the bypass gaseous exhaust material 60 such that its environmental impact is reduced. In these circumstances, the reaction zone 10 may be unable to adequately remove carbon dioxide from the gaseous exhaust material, and this is effected by the another unit operation. In some embodiments, for example, this is done to effect environmental compliance.

The reaction zone parameter which is sensed is any kind of characteristic which provides an indication of the degree to which conditions in the reaction zone 10 are supportive of growth of the phototrophic biomass. In this respect, the sensing of the reaction zone parameter is material to determining whether to modulate an input to the reaction zone 10 in order to promote or optimize growth of the phototrophic biomass. The reaction zone parameter may be an "indication" of a characteristic, in which case the indication can be either a direct or indirect sensing of this characteristic. In some embodiments, for example, the reaction zone parameter is a carbon dioxide supply indication. A carbon dioxide supply indication is an indication of the rate of supply of carbon dioxide to the reaction zone 10. In some embodiments, for example, the carbon dioxide supply indication is a pH within the reaction zone. In some embodiments, for example, the reaction zone parameter is a phototrophic biomass concentration indication. In some embodiments for example, the modulating of a supply of the discharge of the gaseous exhaust material 18 is based on sensing of two or more characteristic indications within the reaction zone 10.

In some embodiments, for example, when at least a fraction of the reaction zone feed material is supplied by a gaseous exhaust material reaction zone supply 24, and when a carbon dioxide supply indication is sensed in the reaction zone 10 which is above a predetermined high carbon dioxide supply value, the modulating of the discharge of the gaseous exhaust material 18 includes: (a) reducing the molar rate of supply, or eliminating the supply, of the gaseous exhaust material reaction zone supply 24 to the reaction zone feed material 22, and (b) effecting the supply, or an increase to the molar rate of supply, of the bypass gaseous exhaust material 60 to the another unit operation.

In some embodiments, for example, when a carbon dioxide supply indication is sensed in the reaction zone 10 which is below a predetermined low carbon dioxide supply value, the modulating of the discharge of the gaseous exhaust material 18 includes: (a) effecting the supply, or an increase to the molar rate of supply, of the gaseous exhaust material reaction zone supply 24 to the reaction zone feed material 22, and (b) effecting elimination of the supply, or a decrease to the molar rate of supply, of the bypass gaseous exhaust material 60 to the another unit operation.

In some embodiments, for example, when at least a fraction of the reaction zone feed material 22 is supplied by a gaseous exhaust material reaction zone supply 24, and when a phototrophic biomass concentration indication is sensed in the reaction zone 10 which is above a predetermined high phototrophic biomass concentration value, the modulating of the discharge of the gaseous exhaust material 18 includes: (a) reducing the molar rate of supply of the gaseous exhaust material reaction zone supply 24 to the reaction zone feed material 22, and (b) increasing the molar rate of supply of the bypass gaseous exhaust material 60 of the gaseous exhaust material 18 to the another unit operation.

In some embodiments, for example, when at least a fraction of the reaction zone feed material 22 is supplied by a gaseous exhaust material reaction zone supply 24, and when a phototrophic biomass concentration indication is sensed in the reaction zone 10 which is below a predetermined low phototrophic biomass concentration value, the modulating of the discharge of the gaseous exhaust material 18 includes: (a) increasing the molar rate of supply of the gaseous exhaust material reaction zone supply 24 to the reaction zone feed material 22, and (b) decreasing the molar rate of supply of the bypass gaseous exhaust material 60 of the gaseous exhaust material 18 to the another unit operation.

In some embodiments, for example, the modulating of the discharge of the gaseous exhaust material 18 is effected while the gaseous exhaust material 18 is being produced by the gaseous exhaust material producing process 20.

In some embodiments, for example, the modulating of the discharge of the gaseous exhaust material 18 is effected while the gaseous exhaust material reaction zone supply 24 is being supplied to the reaction zone feed material 22.

In some embodiments, for example, the modulating of the discharge of the gaseous exhaust material 18 is effected while the reaction zone feed material 24 is being supplied to the reaction zone 10.

In some embodiments, for example, the exposing of the carbon dioxide-enriched phototrophic biomass disposed in the aqueous medium to photosynthetically active light radiation is effected while the modulating of the discharge of the produced gaseous exhaust material 18 is being effected.

As discussed above, in some embodiments, for example, the reaction zone feed material 22 is disposed in fluid communication with the reaction zone 10 through a fluid passage and is supplied as a flow to the reaction zone 10. A flow control element 50 is disposed within the fluid passage and is configured to selectively control the rate of flow of the reaction zone feed material 22 by selectively interfering with the flow of the reaction zone feed material 22 and thereby effecting pressure losses to the flow of the reaction zone feed material 22. In this respect, the reducing of the molar rate of supply, or the eliminating of the supply, of the gaseous exhaust material reaction zone supply 24 to the reaction zone feed material 22 is effected by the flow control element 50. In some embodiments, for example, the controller actuates the flow control element 50 to effect at least one of the reducing of the molar rate of supply, the increasing of the molar rate of supply, the eliminating of the supply, or the initiating of the supply, of the gaseous exhaust material reaction zone supply 24 to the reaction zone feed material 22.

In some embodiments, for example, the flow control element 50 includes a valve. In some embodiments, for example, the flow control element 50 is a three-way valve which also regulates the supply of a supplemental gas-comprising material 48, which is further described below.

In some embodiments, for example, when the reaction zone feed material 22 is supplied to the reaction zone 10 as a flow of the reaction zone feed material 22 which is flowed through the fluid passage, the flowing of the reaction zone feed material 22 is at least partially effected by a prime mover 38. For such embodiments, examples of a suitable prime mover 38 include a blower, a compressor, a pump (for pressurizing liquids including the gaseous exhaust material reaction zone supply 24), and an air pump. In some embodiments, for example, the prime mover 38 is a variable speed blower and the prime mover 38 also functions as the flow control element 50 which is configured to selectively control the flow rate of the reaction zone feed material 22 and define such flow rate.

In some embodiments, for example, the another unit operation is a smokestack 62 which is fluidly coupled to an outlet of the gaseous exhaust material producing process which effects the discharge of the bypass gaseous exhaust material 60. The bypass gaseous exhaust material 60 being discharged from the outlet is disposed at a pressure which is sufficiently high so as to effect flow through the smokestack 62. In some of these embodiments, for example, the flow of the bypass gaseous exhaust material 60 through the smokestack 62 is directed to a space remote from the outlet which discharges the bypass gaseous exhaust material 60 from the gaseous exhaust material producing process 20. Also in some of these embodiments, for example, the bypass gaseous exhaust material 60 is discharged from the outlet when the pressure of the bypass gaseous exhaust material 60 exceeds a predetermined maximum pressure. In such embodiments, for example, the exceeding of the predetermined maximum pressure by the bypass gaseous exhaust material 60 effects an opening of a closure element 64. For example, the closure element 64 is a valve, or a damper, or a stack cap.

In some embodiments, for example, the smokestack 62, which is fluidly coupled to an outlet of the gaseous exhaust material producing process 20, is provided to direct flow of a bypass gaseous exhaust material 60 to a space remote from the outlet which discharges the bypass gaseous exhaust material 60 from the gaseous exhaust material producing process 20, in response to any indication of excessive carbon dioxide, anywhere in the process, so as to mitigate against a gaseous discharge of an unacceptable carbon dioxide concentration to the environment.

In some embodiments, for example, the smokestack 62 is an existing smokestack 62 which has been modified to accommodate lower throughput of gaseous flow as provided by the bypass gaseous exhaust material 60. In this respect, in some embodiments, for example, an inner liner is inserted within the smokestack 62 to accommodate the lower throughput.

In some embodiments, for example, the another unit operation is a separator which effects removal of carbon dioxide from the bypass gaseous exhaust material 60. In some embodiments, for example, the separator is a gas absorber.

In some embodiments, for example, when at least a fraction of the reaction zone feed material 22 is supplied by a gaseous exhaust material reaction zone supply 24, and when a carbon dioxide supply indication is sensed in the reaction zone 10 which is above a predetermined high carbon dioxide supply value, the modulating of the discharge of the gaseous exhaust material 18 includes reducing the molar rate of supply, or eliminating the supply, of the gaseous exhaust material reaction zone supply 24 to the reaction zone feed material 22. Additionally, the process further comprises effecting the supply, or increasing the molar rate of supply, of a supplemental gas-comprising material 48 to the reaction zone feed material 22. The carbon dioxide concentration, if any, of the supplemental gas-comprising material 48 is lower than the carbon dioxide concentration of the gaseous exhaust material reaction zone supply 24. In some embodiments, for example, the modulating of the discharge of the gaseous exhaust material 18 is effected while the gaseous exhaust material 18 is being produced by the gaseous exhaust material producing process 20. In some embodiments, for example, the modulating of the discharge of the gaseous exhaust material 18 is effected while the gaseous exhaust material reaction zone supply 24 is being supplied to the reaction zone feed material 22. In some embodiments, for example, the modulating of the discharge of the gaseous exhaust material 18 is effected while the reaction zone feed material 22 is being supplied to the reaction zone 10. In some of these embodiments, for example, the exposing of the carbon dioxide-enriched phototrophic biomass disposed in the aqueous medium to photosynthetically active light radiation is effected while the modulating is being effected. In some embodiments, for example, the molar supply rate reduction, or the elimination of the supply, of the gaseous exhaust material reaction zone supply 24 to the reaction zone feed material 22 effected by the modulating of the discharge of the gaseous exhaust material 18, co-operates with the supply of the supplemental gas-comprising material 48 to the reaction zone feed material 22 to effect a reduction in the molar rate, or the elimination, of carbon dioxide supply to the reaction zone feed material 22. In some embodiments, for example, the modulating of the discharge of the gaseous exhaust material 18 further effects the supply, or an increase to the molar rate of supply, from the discharged gaseous exhaust material, of a bypass gaseous exhaust material 60 to another unit operation which converts the bypass gaseous exhaust material 60 such that its environmental impact is reduced. In some embodiments, for example, the reaction zone feed material 22 is disposed in fluid communication with the reaction zone 10 through a fluid passage, and the reaction zone feed material is supplied to the reaction zone 10 as a flow which is flowed through the fluid passage. In this respect, in some embodiments, the reaction zone feed material being supplied to the reaction zone 10 is a reaction zone feed material flow, and the reducing (of the molar rate of supply of the gaseous exhaust material reaction zone supply 24 to the reaction zone feed material 22) effects a reduction in the fraction of the reaction zone feed material flow which is a gaseous exhaust material reaction zone supply flow.

In some embodiments, for example, when at least a fraction of the reaction zone feed material is supplied by a gaseous exhaust material reaction zone supply 24, and when a carbon dioxide supply indication is sensed in the reaction zone 10 which is above a predetermined high carbon dioxide supply value, the modulating of the discharge of the gaseous exhaust material 18 includes reducing the molar rate of supply, or eliminating the supply, of the gaseous exhaust material reaction zone supply 24 to the reaction zone feed material 22. Additionally, the process further includes effecting the supply, or increasing the molar rate of supply, of a supplemental gas-comprising material 48 to the reaction zone feed material 22 for at least partially compensating for the reduction in molar supply rate of material, or the elimination of any material supply, to the reaction zone feed material 22 effected by the modulating of the discharge of the gaseous exhaust material 18. The molar supply rate reduction, or the elimination of the supply, of the gaseous exhaust material reaction zone supply 24 to the reaction zone feed material 22 effected by the modulating of the discharge of the gaseous exhaust material 18 co-operates with the supply of the supplemental gas-comprising material 48 to the reaction zone feed material 22 to effect a reduction in the molar rate, or the elimination, of carbon dioxide supply to the reaction zone feed material 22. In some embodiments, for example, the modulating is effected while the gaseous exhaust material 18 is being produced by the gaseous exhaust material producing process 20. In some embodiments, for example, the modulating of the discharge of the gaseous exhaust material 18 is effected while the gaseous exhaust material reaction zone supply 24 is being supplied to the reaction zone feed material 22. In some embodiments, for example, the modulating of the discharge of the gaseous exhaust material 18 is effected while the reaction zone feed material 22 is being supplied to the reaction zone 10. In some of these embodiments, for example, the exposing of the carbon dioxide-enriched phototrophic biomass disposed in the aqueous medium to photosynthetically active light radiation is effected while the modulating is being effected. In some embodiments, for example, the concentration of carbon dioxide, if any, in the supplemental gas-comprising material 48, is less than the concentration of carbon dioxide in the gaseous exhaust material reaction zone supply 24. In some embodiments, for example, the reaction zone feed material 22 being supplied to the reaction zone 10 is flowed to the reaction zone 10 to effect the supply of the reaction zone feed material 22 to the reaction zone 10, and the compensation, for the reduction in molar supply rate of material, or the elimination of any material supply, to the reaction zone feed material 22 effected by the modulating of the discharge of the gaseous exhaust material 18, as effected by the supply of the supplemental gas-comprising material 48, effects substantially no change to the molar rate of flow of reaction zone feed material 22 to the reaction zone 10. In some embodiments, for example, the modulating of the discharge of the gaseous exhaust material 18 further effects the supply, or an increase to the molar rate of supply, from the discharged gaseous exhaust material, of a bypass gaseous exhaust material 60 to another unit operation which converts the bypass gaseous exhaust material 60 such that its environmental impact is reduced. In some embodiments, for example, the reaction zone feed material 22 is disposed in fluid communication with the reaction zone 10 through a fluid passage and the reaction zone feed material 22 is supplied to the reaction zone 10 as a flow which is flowed through the fluid passage. In this respect, the reaction zone feed material 22 being supplied to the reaction zone 10 is a reaction zone feed material flow, and the reducing (of the molar rate of supply of the gaseous exhaust material reaction zone supply 24 to the reaction zone feed material 22) effects a reduction in the fraction of the flow of the reaction zone feed material 22 which is a flow of a gaseous exhaust material reaction zone supply 24.

The combination of: (a) the molar supply rate reduction, or the elimination of the supply, of the gaseous exhaust material reaction zone supply 24 to the reaction zone feed material 22, and (b) the supplying, or the increasing of the supplying, of a supplemental gas-comprising material 48 to the reaction zone feed material 22, mitigates against the reduced agitation of the reaction zone 10 attributable to the reduction in the molar rate of supply, or elimination of the supply, of the gaseous exhaust material reaction zone supply 24 to the reaction zone feed material 22.

In some embodiments, for example, the molar rate of carbon dioxide being supplied, if any, in the supplemental gas-comprising material 48, is sufficiently low such that the supply of the supplemental gas-comprising material 48, in co-operation with the molar supply rate reduction, or the elimination of supply, of the gaseous exhaust material reaction zone supply 24, effects a reduction in the molar rate of carbon dioxide being supplied to the reaction zone feed material 22.

In some embodiments, for example, the reaction zone feed material 22 is flowed to the reaction zone 10 and effects agitation of material in the reaction zone such that any difference in phototrophic biomass concentration between two points in the reaction zone 10 is less than 20%. In some embodiments, for example, the effected agitation is such that any difference in phototrophic biomass concentration between two points in the reaction zone 10 is less than 10%.

In some embodiments, for example, the flow control element 50 is a three-way valve which also regulates the supply of the supplemental gas-comprising material 48, and is actuated by the controller in response to carbon dioxide concentration indications which are sensed within the reaction zone 10.

In some embodiments, for example, the supplemental gas-comprising material 48 is a gaseous material. In some of these embodiments, for example, the supplemental gas-comprising material 48 includes a dispersion of gaseous material in a liquid material. In some of these embodiments, for example, the supplemental gas-comprising material 48 includes air. In some of these embodiments, for example, the supplemental gas-comprising material 48 is provided as a flow.

In some embodiments, for example, the supply, or increasing the molar rate of supply, of a supplemental gas-comprising material 48 to the reaction zone feed material 22 is effected while the gaseous exhaust material 18 is being produced by the gaseous exhaust material producing process 20. In some embodiments, for example, the supply, or increasing the molar rate of supply, of a supplemental gas-comprising material 48 to the reaction zone feed material 22 is effected while the gaseous exhaust material reaction zone supply 24 is being supplied to the reaction zone feed material 22. In some embodiments, for example, the supply, or increasing the molar rate of supply, of a supplemental gas-comprising material 48 to the reaction zone feed material 22 is effected while the reaction zone feed material 22 is being supplied to the reaction zone 10. In some of these embodiments, for example, the exposing of the carbon dioxide-enriched phototrophic biomass disposed in the aqueous medium to photosynthetically active light radiation is effected while the supply, or increasing the molar rate of supply, of a supplemental gas-comprising material 48 to the reaction zone feed material 22 is effected.

In some embodiments, for example, when the reaction zone parameter is a carbon dioxide supply indication, the carbon dioxide supply indication is a pH. In this respect, for example, the sensing of a reaction zone parameter includes sensing a pH in the reaction zone 10. In such embodiments, for example, the pH is sensed in the reaction zone 10 with a pH sensor 46. In some embodiments, for example, upon sensing a pH in the reaction zone 10 which is below a predetermined low pH value (i.e. the predetermined high carbon dioxide supply indication value), the pH sensor 46 transmits a low pH signal to the controller, and the controller responds by effecting decreasing of the molar supply rate of, or effecting elimination of supply of, carbon dioxide supply to the reaction zone feed material 22. In some embodiments, for example, this is effected by effecting decreasing of the molar supply rate of, or effecting elimination of supply of, the gaseous exhaust material reaction zone supply 24 being to the reaction zone feed material 22, such as by using flow control element 50, as described above. The predetermined low pH value depends on the phototrophic organisms of the biomass. In some embodiments, for example, the predetermined low pH value can be as low as 4.0. In some embodiments, for example, upon sensing a pH in the reaction zone 10 which is above a predetermined high pH value (i.e. the predetermined low carbon dioxide supply indication value), the pH sensor 46 transmits a high pH signal to the controller, and the controller responds by effecting increasing of the molar supply rate of, or effecting initiation of supply of, carbon dioxide to the reaction zone feed material. In some embodiments, for example, this is effected by effecting increasing of the molar supply rate of, or effecting initiation of supply of, the gaseous exhaust material reaction zone supply 24 to the reaction zone feed material 22, such as by using flow control element 50, as described above. The predetermined high pH value depends on the phototrophic organisms of the biomass.

Operating with a pH in the reaction zone 10 which is above the predetermined high pH (indicating an insufficient molar rate of supply of carbon dioxide to the reaction zone feed material 22), or which is below the predetermined low pH (indicating an excessive molar rate of supply of carbon dioxide to the reaction zone feed material 22), effects less than optimal growth of the phototrophic biomass, and, in the extreme, could effect death of the phototrophic biomass.

In some embodiments, for example, when the characteristic indication is a phototrophic biomass concentration indication, the phototrophic biomass concentration indication is sensed by a cell counter. For example, a suitable cell counter is an AS-16F Single Channel Absorption Probe supplied by optek-Danulat, Inc. of Germantown, Wis., U.S.A. Other suitable devices for sensing a phototrophic biomass concentration indication include other light scattering sensors, such as a spectrophotometer. As well, the phototrophic biomass concentration indication can be sensed manually, and then input manually into the controller for effecting the desired response.

In some embodiments, for example, it is desirable to control concentration of the phototrophic biomass in the reaction zone 10. For example, higher overall yield of harvested phototrophic biomass is effected when the concentration of the phototrophic biomass in the reaction zone 10 is controlled at a predetermined concentration or within a predetermined concentration range. In some embodiments, for example, upon sensing a phototrophic biomass concentration indication in the reaction zone 10 which is below the predetermined low phototrophic biomass concentration value, the cell counter transmits a low phototrophic biomass concentration signal to the controller, and the controller responds by effecting increasing of the molar supply rate of, or effecting initiation of supply of, carbon dioxide to the reaction zone 10. In some embodiments, for example, this is effected by effecting increasing of the molar supply rate of, or effecting initiation of supply of, the gaseous exhaust material reaction zone supply 24 to the reaction zone feed material 22, such as by using flow control element 50, as described above. The predetermined low phototrophic biomass concentration value depends on the phototrophic organisms of the biomass. In some embodiments, for example, upon sensing a phototrophic biomass concentration indication in the reaction zone 10 which is above the predetermined high phototrophic biomass concentration value, the cell counter transmits a high phototrophic biomass concentration signal to the controller, and the controller responds by effecting decreasing of the molar supply rate of, or effecting elimination of supply of, carbon dioxide to the reaction zone feed material 22. In some embodiments, for example, this is effected by effecting decreasing of the molar supply rate of, or effecting elimination of supply of, the gaseous exhaust material reaction zone supply 24 to the reaction zone feed material 22, such as by using flow control element 50, as described above. The predetermined high phototrophic biomass concentration value depends on the phototrophic organisms of the biomass.

In some embodiments, for example, the phototrophic biomass is recovered or harvested. With respect to those embodiments where the reaction zone 10 is disposed in a photobioreactor 12, in some of these embodiments, the upper portion of phototrophic biomass suspension in the reaction zone 10 overflows the photobioreactor 12 (for example, the phototrophic biomass is discharged through an overflow port of the photobioreactor 12) to provide the harvested biomass 58. In those embodiments where the phototrophic biomass includes algae, the harvesting is effected at a rate which matches the growth rate of the algae, in order to mitigate shocking of the algae in the reaction zone 10. With respect to some embodiments, for example, the harvesting is controlled through the rate of supply of supplemental aqueous material supply 44, which influences the displacement from the photobioreactor 12 of the photobioreactor overflow 59 (including the harvested biomass 58) from the photobioreactor 12. In other embodiments, for example, the harvesting is controlled with a valve disposed in a fluid passage which is fluidly communicating with an outlet of the photobioreactor 12.

In some embodiments, for example, the harvesting is effected continuously. In other embodiments, for example, the harvesting is effected periodically. In some embodiments, for example, the harvesting is designed such that the concentration of the biomass in the harvested biomass 58 is relatively low. In those embodiments where the phototrophic biomass includes algae, it is desirable, for some embodiments, to harvest at lower concentrations to mitigate against sudden changes in the growth rate of the algae in the reaction zone 10. Such sudden changes could effect shocking of the algae, which thereby contributes to lower yield over the longer term. In some embodiments, where the phototrophic biomass is algae and, more specifically, scenedesmus obliquus, the concentration of this algae in the harvested biomass 58 could be between 0.5 and 3 grams per liter. The desired concentration of the harvested algae depends on the strain of algae such that this concentration range changes depending on the strain of algae. In this respect, in some embodiments, maintaining a predetermined water content in the reaction zone is desirable to promote the optimal growth of the phototrophic biomass, and this can also be influenced by controlling the supply of the supplemental aqueous material supply 44.

The harvested biomass 58 includes water. In some embodiments, for example, the harvested biomass 58 is supplied to a separator 52 for effecting removal of at least a fraction of the water from the harvested biomass 58 to effect production of an intermediate concentrated biomass product 34 and a recovered aqueous material 72 (generally, water). In some embodiments, for example, the separator 52 is a high speed centrifugal separator 52. Other suitable examples of a separator 52 include a decanter, a settling vessel or pond, a flocculation device, or a flotation device. In some embodiments, the recovered aqueous material 72 is supplied to a return pond 28 for re-use by the process.

In some embodiments, for example, after harvesting, and before being supplied to the separator 52, the harvested biomass 58 is supplied to a harvest pond 54. The harvest pond 54 functions both as a buffer between the photobioreactor 12 and the separator 52, as well as a mixing vessel in cases where the harvest pond 54 receives different biomass strains from multiple photobioreactors. In the latter case, customization of a blend of biomass strains can be effected with a predetermined set of characteristics tailored to the fuel type or grade that will be produced from the blend.

As described above, the return pond 28 provides a source of supplemental aqueous material supply 44 for the reaction zone 10. Loss of water is experienced in some embodiments as moisture in the final biomass product 36, as well as through evaporation in the dryer 32. The supplemental aqueous material in the return pond 28, which is recovered from the process, can be supplied to the reaction zone 10 as the supplemental aqueous material supply 44. In some embodiments, for example, the supplemental aqueous material supply 44 is supplied to the reaction zone 10 with a pump. In other embodiments, the supply can be effected by gravity, if the layout of the process equipment of the system, which embodies the process, permits. As described above, the supplemental aqueous material recovered from the process includes at least one of: (a) aqueous material 70 which has been condensed from the reaction zone feed material 22 while the reaction zone feed material 22 is being cooled before being supplied to the reaction zone 10, and (b) aqueous material 72 which has been separated from the discharged product 59. In some embodiments, for example, the supplemental aqueous material supply 44 is supplied to the reaction zone 10 to influence overflow of the photobioreactor overflow 59 by increasing the upper level of the contents of the reaction zone 10. In some embodiments, for example, the supplemental aqueous material supply 44 is supplied to the reaction zone 10 to influence a desired predetermined concentration of phototrophic biomass to the reaction zone by diluting the contents of the reaction zone.

Examples of specific structures which can be used as a return pond 28 by allowing for containment of aqueous material recovered from the process, as above-described, include, without limitation, tanks, ponds, troughs, ditches, pools, pipes, tubes, canals, and channels.

In some embodiments, for example, the supplying of the supplemental aqueous material supply to the reaction zone 10 is effected while the gaseous exhaust material 18 is being produced by the gaseous exhaust material producing process 20. In some embodiments, for example, the supplying of the supplemental aqueous material supply to the reaction zone is effected while the gaseous exhaust material reaction zone supply 24 is being supplied to the reaction zone feed material 22. In some embodiments, for example, the supplying of the supplemental aqueous material supply to the reaction zone 10 is effected while the reaction zone feed material 24 is being supplied to the reaction zone 10. In some embodiments, for example, the exposing of the carbon dioxide-enriched phototrophic biomass disposed in the aqueous medium to photosynthetically active light radiation is effected while the supplying of the supplemental aqueous material supply to the reaction zone 10 is being effected.

As described above, in some embodiments, for example, the discharging of the product 59 is effected by an overflow of the at least a fraction of the contents of the reaction zone 10 of the photobioreactor 12. When the upper level of the contents of the reaction zone 10 within the photobioreactor 12 becomes disposed below a predetermined minimum level, the supplying of, or an increase to the molar rate of supply, of the supplemental aqueous material supply 44 (which has been recovered from the process) is effected to the reaction zone 10. In some of these embodiments, for example, a level sensor 76 is provided, and when the level sensor 76 senses a predetermined low level of the upper level of the contents of the reaction zone 10 within the photobioreactor 12, the level sensor transmits a low level signal to the controller. When the supply of the supplemental aqueous material supply 44 to the reaction zone 10 is effected by a pump, the controller actuates the pump to effect commencement of supply, or an increase to the rate of supply, of the supplemental aqueous material supply 44 to the reaction zone 10. When the supply of the supplemental aqueous material supply 44 to the reaction zone 10 is effected by gravity, the controller actuates the opening of a control valve to effect commencement of supply, or an increase to the rate of supply, of the supplemental aqueous material supply 44 to the reaction zone 10.

In other embodiments, for example, where the harvesting is controlled with a valve disposed in a fluid passage which is fluidly communicating with an outlet of the photobioreactor 12, algae concentration in the reaction zone is sensed by a cell counter, such as the cell counters described above. The sensed algae concentration is transmitted to the controller, and the controller responds by actuating a pump 281 to effect supply of the supplemental aqueous material supply 44 to the reaction zone 10.

In some embodiments, for example, a source of additional make-up water 68 is provided to mitigate against circumstances when the supplemental aqueous material supply 44 is insufficient to make-up for water which is lost during operation of the process. In this respect, in some embodiments, for example, the supplemental aqueous material supply 44 is mixed with the reaction zone feed material 22 in the sparger 40. Conversely, in some embodiments, for example, accommodation for draining of the return pond 28 to drain 66 is provided to mitigate against the circumstances when aqueous material recovered from the process exceeds the make-up requirements.

In some embodiments, for example, a reaction zone gaseous effluent 80 is discharged from the reaction zone 10. At least a fraction of the reaction zone gaseous effluent 80 is recovered and supplied to a reaction zone 110 of a combustion process unit operation 100. As a result of the photosynthesis being effected in the reaction zone 10, the reaction zone gaseous effluent 80 is rich in oxygen relative to the gaseous exhaust material reaction zone supply 24. The gaseous effluent 80 is supplied to the combustion zone 110 of a combustion process unit operation 100 (such as a combustion zone 110 disposed in a reaction vessel), and, therefore, functions as a useful reagent for the combustion process being effected in the combustion process unit operation 100. The reaction zone gaseous effluent 80 is contacted with combustible material (such as carbon-comprising material) in the combustion zone 100, and a reactive process is effected whereby the combustible material is combusted. Examples of suitable combustion process unit operations 100 include those in a fossil fuel-fired power plant, an industrial incineration facility, an industrial furnace, an industrial heater, an internal combustion engine, and a cement kiln.

In some embodiments, for example, the contacting of the recovered reaction zone gaseous effluent with a combustible material is effected while the gaseous exhaust material is being produced by the gaseous exhaust material producing process. In some embodiments, for example, the contacting of the recovered reaction zone gaseous effluent with a combustible material is effected while the gaseous exhaust material reaction zone supply is being supplied to the reaction zone feed material. In some embodiments, for example, the contacting of the recovered reaction zone gaseous effluent with a combustible material is effected while the reaction zone feed material is being supplied to the reaction zone. In some embodiments, for example, the exposing of the carbon dioxide-enriched phototrophic biomass disposed in the aqueous medium to photosynthetically active light radiation is effected while the contacting of the recovered reaction zone gaseous effluent with a combustible material is being effected.

The intermediate concentrated biomass product 34 is supplied to a dryer 32 which supplies heat to the intermediate concentrated biomass product 34 to effect evaporation of at least a fraction of the water of the intermediate concentrated biomass product 34, and thereby effect production of a final biomass product 36. As discussed above, in some embodiments, the heat supplied to the intermediate concentrated biomass product 34 is provided by a heat transfer medium 30 which has been used to effect the cooling of the reaction zone feed material 22 prior to supply of the reaction zone feed material 22 to the reaction zone 10. By effecting such cooling, heat is transferred from the reaction zone feed material 22 to the heat transfer medium 30, thereby raising the temperature of the heat transfer medium 30. In such embodiments, the intermediate concentrated biomass product 34 is at a relatively warm temperature, and the heat requirement to effect evaporation of water from the intermediate concentrated biomass product 34 is not significant, thereby rendering it feasible to use the heated heat transfer medium 30 as a source of heat to effect the drying of the intermediate concentrated biomass product 34. As discussed above, after heating the intermediate concentrated biomass product 34, the heat transfer product, having lost some energy and becoming disposed at a lower temperature, is recirculated to the heat exchanger 26 to effect cooling of the reaction zone feed material 22. The heating requirements of the dryer 32 is based upon the rate of supply of intermediate concentrated biomass product 34 to the dryer 32. Cooling requirements (of the heat exchanger 26) and heating requirements (of the dryer 32) are adjusted by the controller to balance the two operations by monitoring flowrates and temperatures of each of the reaction zone feed material 22 and the rate of harvesting of the harvested biomass 58.

In some embodiments, changes to the phototrophic biomass growth rate related to changes to the rate of supply of the gaseous exhaust material reaction zone supply 24 to the reaction zone material feed 22 are realized after a significant time lag (for example, in some cases, more than three (3) hours, and sometimes even longer) from the time when the change is effected to the rate of supply of the gaseous exhaust material reaction zone supply 24 to the reaction zone feed material 22. In comparison, changes to the thermal value of the heat transfer medium 30, which are based on the changes in the rate of supply of the gaseous exhaust material reaction zone supply 24 to the reaction zone feed material 22, are realized more quickly. In this respect, in some embodiments, a thermal buffer is provided for storing any excess heat (in the form of the heat transfer medium 30) and introducing a time lag to the response of the heat transfer characteristics of the dryer 32 to the changes in the gaseous exhaust material reaction zone supply 24. Alternatively, an external source of heat may be required to supplement heating requirements of the dryer 32 during transient periods of supply of the gaseous exhaust material reaction zone supply 24 to the reaction zone material 22. The use of a thermal buffer or additional heat may be required to accommodate changes to the rate of growth of the phototrophic biomass, or to accommodate start-up or shutdown of the process. For example, if growth of the phototrophic biomass is decreased or stopped, the dryer 32 can continue operating by using the stored heat in the buffer until it is consumed, or, in some embodiments, use a secondary source of heat.

In the above description, for purposes of explanation, numerous details are set forth in order to provide a thorough understanding of the present disclosure. However, it will be apparent to one skilled in the art that these specific details are not required in order to practice the present disclosure. Although certain dimensions and materials are described for implementing the disclosed example embodiments, other suitable dimensions and/or materials may be used within the scope of this disclosure. All such modifications and variations, including all suitable current and future changes in technology, are believed to be within the sphere and scope of the present disclosure. All references mentioned are hereby incorporated by reference in their entirety.

The invention claimed is:

1. A process of growing a phototrophic biomass in a reaction zone, wherein the reaction zone includes an operative reaction mixture, wherein the operative reaction mixture includes the phototrophic biomass disposed in an aqueous medium, comprising:

producing gaseous exhaust material with a gaseous exhaust material producing process, wherein the gaseous exhaust material includes carbon dioxide;

supplying a supplemental gaseous dilution agent to the gaseous exhaust material to produce a diluted gaseous exhaust material, wherein the supplemental gaseous dilution agent has a carbon dioxide concentration that is less than the carbon dioxide concentration of the gaseous exhaust material and wherein the supplying of the supplemental gaseous dilution agent to the gaseous exhaust material is effected in response to sensing of a carbon dioxide concentration in the gaseous exhaust material being discharged from the carbon dioxide producing process which is greater than a predetermined maximum carbon dioxide concentration value;

supplying the diluted gaseous exhaust material to the reaction zone such that carbon dioxide is received by the phototrophic biomass so as to provide a carbon dioxide-enriched phototrophic biomass in the aqueous medium; and exposing the carbon dioxide-enriched phototrophic biomass disposed in the aqueous medium to photosynthetically active light radiation so as to effect photosynthesis.

2. The process as claimed in claim 1;
wherein the supplying of the supplemental gaseous dilution agent to the gaseous exhaust material provides a carbon dioxide concentration in the diluted gaseous exhaust material being supplied to the reaction zone which is below a predetermined maximum carbon dioxide concentration value.

3. The process as claimed in claim 1;
wherein the supplying of the supplemental gaseous dilution agent to the gaseous exhaust material effects dilution of the gaseous exhaust material with respect to carbon dioxide concentration.

4. The process as claimed in claim 1;
wherein the supplying of the supplemental gaseous dilution agent to the gaseous exhaust material effects a reduction of the carbon dioxide concentration of the gaseous exhaust material.

5. The process as claimed in claim 1;
wherein the gaseous exhaust material includes an upstream gaseous exhaust material and a downstream gaseous exhaust material, wherein the downstream gaseous exhaust material is downstream of the upstream gaseous exhaust material relative to the reaction zone;
and wherein the supplemental gaseous dilution agent is admixed with the upstream gaseous exhaust material to provide the downstream gaseous exhaust material such that the concentration of carbon dioxide in the downstream gaseous exhaust material is less than the concentration of carbon dioxide in the upstream gaseous exhaust material.

6. The process as claimed in claim 1;
wherein the supplying of the gaseous exhaust material with a supplemental gaseous dilution agent is effected while the gaseous exhaust material is being produced by the gaseous exhaust material producing process.

7. The process as claimed in claim 1;
wherein the supplying of the gaseous exhaust material with a supplemental gaseous dilution agent is effected while the gaseous exhaust material is being supplied to the reaction zone.

8. The process as claimed in claim 1;
wherein the exposing of the carbon dioxide-enriched phototrophic biomass disposed in the aqueous medium to photosynthetically active light radiation is effected while the supplying of the gaseous exhaust material with a supplemental gaseous dilution agent is being effected.

9. The process as claimed in claim 1;
wherein the supplemental gaseous dilution agent is gaseous material.

10. The process as claimed in claim 1;
wherein the supplemental gaseous dilution agent includes air.

11. The process as claimed in claim 1;
wherein the gaseous exhaust material is being supplied to the reaction zone as a flow; and
wherein the supplemental gaseous dilution agent is being supplied to the gaseous exhaust material as a flow.

12. The process as claimed in claim 1;
wherein the supplying of the supplemental gaseous dilution agent is effected while the gaseous exhaust material is being produced by the gaseous exhaust material producing process.

13. The process as claimed in claim 1;
wherein the supplying of the supplemental gaseous dilution agent is effected while the diluted gaseous exhaust material is being supplied to the reaction zone.

14. The process as claimed in claim 13;
wherein the exposing of the carbon dioxide-enriched phototrophic biomass disposed in the aqueous medium to photosynthetically active light radiation is effected while the supplying of the supplemental gaseous dilution agent is being effected.

* * * * *